United States Patent
Voss

(10) Patent No.: US 12,419,587 B2
(45) Date of Patent: Sep. 23, 2025

(54) UP-SAMPLING OF SIGNALS BY ANALYTIC PHASE PROJECTION

(71) Applicant: Cornell University, Ithaca, NY (US)

(72) Inventor: Henning U. Voss, New York, NY (US)

(73) Assignee: Cornell University, Ithaca, NY (US)

( * ) Notice: Subject to any disclaimer, the term of this patent is extended or adjusted under 35 U.S.C. 154(b) by 958 days.

(21) Appl. No.: 17/046,371

(22) PCT Filed: Apr. 10, 2019

(86) PCT No.: PCT/US2019/026775
§ 371 (c)(1),
(2) Date: Oct. 9, 2020

(87) PCT Pub. No.: WO2019/199960
PCT Pub. Date: Oct. 17, 2019

(65) Prior Publication Data
US 2021/0128077 A1 May 6, 2021

Related U.S. Application Data

(60) Provisional application No. 62/655,970, filed on Apr. 11, 2018.

(51) Int. Cl.
*A61B 5/00* (2006.01)
*A61B 5/055* (2006.01)
*A61B 5/31* (2021.01)

(52) U.S. Cl.
CPC ............ *A61B 5/7289* (2013.01); *A61B 5/055* (2013.01); *A61B 5/31* (2021.01); *A61B 5/7253* (2013.01)

(58) Field of Classification Search
CPC ......... A61B 5/7289; A61B 5/055; A61B 5/31; A61B 5/7253; A61B 5/369; A61B 5/318;
(Continued)

(56) References Cited

U.S. PATENT DOCUMENTS

2005/0059880 A1  3/2005  Mathias et al.
2008/0246475 A1  10/2008 Adachi
(Continued)

FOREIGN PATENT DOCUMENTS

| EP | 1 999 480 B1 | 12/2008 |
|---|---|---|
| EP | 2 349 008 | 8/2011 |
| JP | 2004-000356 | 1/2004 |
| JP | 2016-147055 | 8/2016 |
| WO | WO-2015/112804 | 7/2015 |

OTHER PUBLICATIONS

Tokariev, A. Phase synchrony in the early preterm EEG: development of methods for estimating synchrony in both oscillations and events. NeuroImage 60: 1562-1573. (Year: 2012).*

(Continued)

*Primary Examiner* — Olivia M. Wise
*Assistant Examiner* — Robert J. Kallal
(74) *Attorney, Agent, or Firm* — Foley & Lardner LLP

(57) ABSTRACT

The systems and methods of the present disclosure address the problem of up-sampling an insufficiently sampled signal of numbers or images that does not yield interpretable data. A computing device may acquire from a sensor, a reference signal and a quasi-periodic signal of a subject over a predefined time period. The reference signal may have a fixed sampling rate. The quasi-periodic signal may have a variable sampling rate. The computing device may filter, using a band-pass filter, the reference signal to obtain a monocomponent signal. The computing device may determine, by applying a Hilbert transform on the monocomponent signal, an analytic phase. The computing device may generate a phase projected signal from the quasi-periodic signal based on the analytic phase. The phase projected signal may have a plurality of data points of the quasi-periodic signal across the predefined time period mapped to a predefined phase interval.

24 Claims, 14 Drawing Sheets

(58) Field of Classification Search
CPC ........ A61B 2576/023; A61B 2576/026; G01R 33/5608; G01R 33/5635; G01R 33/5673; G16H 30/40
See application file for complete search history.

(56) References Cited

U.S. PATENT DOCUMENTS

2015/0287222 A1    10/2015    Zhao et al.
2016/0370444 A1    12/2016    Peng et al.

OTHER PUBLICATIONS

Yuan, Z. Adaptive sampling for ECG detection based on compression dictionary. Journal of Semiconductor Technology and Science 13(6): 608-616. (Year: 2013).*

Sun L & Hinrichs H. Simultaneously recorded EEG-fMRI: removal of gradient artifacts by subtraction of head movement related average artifact waveforms. Human Brain Mapping 30: 3361-3377. (Year: 2009).*

Foreign Search Report on EP 19784688.4 DTD Dec. 15, 2021, 15 pages.

International Preliminary Report on Patentability on PCT PCT/US2019/026775 DTD Oct. 22, 2020, 6 pages.

Voss, "Hypersampling of psuedo-periodic signals by analtyic phase projection", Cornell University Library, Apr. 27, 2018 (Year: 2018), 10 pages.

Voss, et al., "Hypersampling of psuedo-periodic signals by analytic phase projection", Computers in Biology and Medicine, vol. 98, May 16, 2018, pp. 159-167 (Year: 2018).

Chen, et al., "Amplitudes of mono-component signals and the generalized sampling functions", Signal Processing, 2014, vol. 94, pp. 255-263.

International Search Report and Written Opinion in International Patent Application No. PCT/US2019/026775 dated Jul. 23, 2019.

* cited by examiner

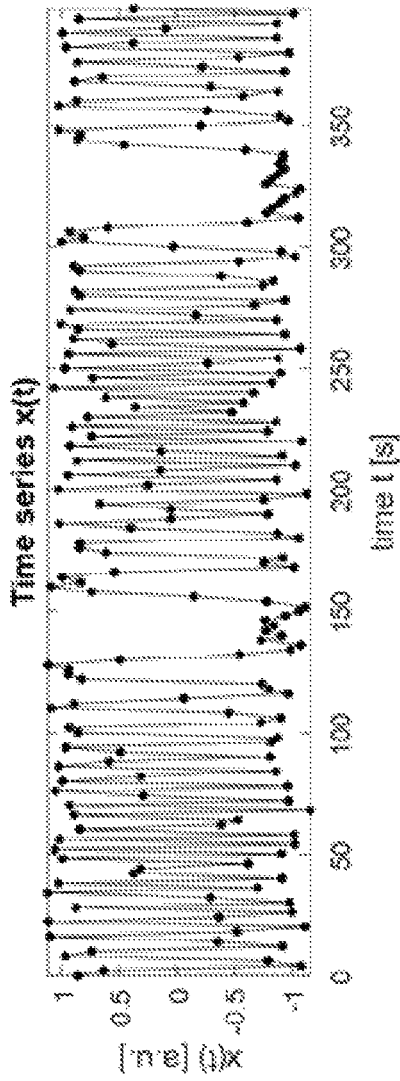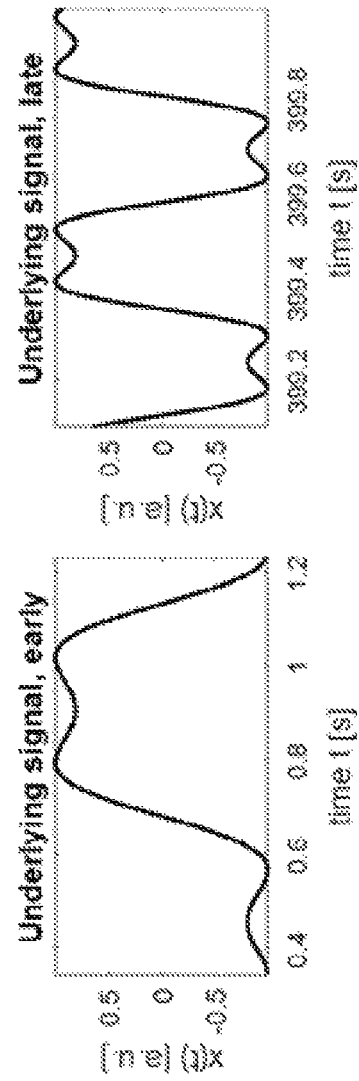
FIG. 4A
FIG. 4B

UP-SAMPLING OF SIGNALS BY ANALYTIC PHASE PROJECTION

CROSS REFERENCE TO RELATED APPLICATION

This application is a U.S. National Stage Application under 35 U.S.C. § 371 of International Patent Application No. PCT/US2019/026775, filed on Apr. 10, 2019, which claims priority to U.S. Provisional Patent Application No. 62/655,970 entitled "UP-SAMPLING OF SIGNALS BY ANALYTIC PHASE PROJECTION," filed Apr. 11, 2018, each of which are herein incorporated by reference in their entireties for all purposes.

BACKGROUND

Up-sampling to a higher sampling rate can provide information that may not be visible in the original signal. To resolve improper renderings of a time-resolved series of images (or "movie"), retrospective gating may be employed. Retrospective gating, however, may be severely restricted in the number of applications that the technique may be used.

SUMMARY

Various embodiments of the disclosure relate to a more efficient up-sampling approach referred to as "hypersampling." Hypersampling comprises an up-sampling of an undersampled time series by using analytic phase projection (APP). An "undersampled" signal here refers to a signal whose sampling rate is not sufficient to resolve the time variability of the object under investigation. Whereas in retrospective gating a recurring template is identified from the reference signal, in hypersampling the continuous phase underlying the quasi-periodic reference signal is identified from the reference signal. This phase estimate may then be used for APP.

In various embodiments, the present disclosure addresses the problem of up-sampling an insufficiently sampled signal of numbers or images that does not yield interpretable data. A procedure to up-sample an insufficiently sampled time series of numbers or images is detailed herein. It is based on the projection of its values to the analytic phase of a reference signal, the APP. The analytic phase may be obtained from the Hilbert transform of the reference signal. For quasi-periodic time series, an up-sampling factor of several orders of magnitudes can be achieved. Application of this disclosure may include imaging the pulsations of the vascular system including the brain and heart by using MM and a pulse reference signal. Another application may include imaging the source of cerebral EEG signals by using functional MM images of the brain and the EEG signals as reference. More generally, this procedure can be used in all applications where conventional (template-based) retrospective gating has been used so far. The analytic phase projection then replaces the template and improves gating accuracy, and provides a means to up-sample the signal.

By up-sampling to a higher sampling rate, information that may not be visible in the original signal may be ascertained. For example, in Mill imaging of the beating heart, the sampling rate of the Mill image acquisition is too low to obtain a time-resolved series of images (or "movie") of the beating heart. The incoming images may provide randomly ordered snapshots of the heart, which, if played out as a movie, may not properly render the beating heart. In order to solve this, the method of retrospective gating usually is employed. In retrospective gating, a sufficiently sampled reference signal is acquired and the onset of cycles extracted from it by matching to a cycle template. Then, the insufficiently sampled signal is re-ordered to match the cycle signal obtained from the reference signal. For example, in Mill of the beating heart, the reference signal can be an ECG signal of the heart or a pulse oximetry signal from a finger of the subject, which both can be sampled at a sufficient rate to allow for a proper definition of the cardiac cycle by matching a cardiac pulse template to it. The cycle-matched or retrospectively gated images then define a smooth signal of images of the beating heart, which can be assembled into a movie of the beating heart over one cycle. Playing this movie in a repeat loop then provides the impression of a continuously beating heart.

In certain applications, there may be only view noninvasive imaging modalities to measure vascular dynamics, and their use is often restricted to certain parts of the body. For example, the waves used in ultrasound sonography cannot penetrate the skull sufficiently in order to obtain high-resolution images. There are some MM based procedures that image anatomy of the cerebrovascular system such as MM angiography, but these methods are based on static images and do not address the characterization of the pulse waves. There are also dynamic Mill modalities such as arterial spin labeling and phase coherence imaging that can image arterial blood flow in the brain, but they image mainly the non-pulsatory part of cerebral blood flow. In these methods, the signal variability is orders of magnitude slower than in the signals that can be investigated with the present disclosure. Very recently, 4D flow imaging has been emerging as a modality to measure pulse wave velocity, too. So far it has not been applied to the brain without the use of contrast agent but only to much larger vessels outside of the brain, for example the aorta.

Retrospective gating may be replaced by analytic phase projection in order to become easier applicable (removal of the template-matching step) or for a widened applicability (band-limited signals vs. quasi-periodic signals), thereby increasing the number of different applications.

Various embodiments of the disclosure relate to a method of performing up-sampling of signals by analytic phase projection. The method may be implemented using a computing system. The method may comprise acquiring, via one or more sensors, a reference signal and a time series of number or images of a subject. The reference signal and time series may be acquired over a predefined time period. The method may also comprise filtering the reference signal to obtain a monocomponent signal. The method may moreover comprise determining an analytic phase. The analytic phase may be determined by performing a transform operation on the monocomponent signal. The method may additionally comprise generating a phase projected signal from the time series based on the analytic phase. The method may further comprise displaying phase projected signal for an application.

In one or more implementations, the time series is a quasi-periodic signal.

In one or more implementations, the time series and the reference signal may be acquired substantially simultaneously during the predefined time interval.

In one or more implementations, the method may furthermore comprise preprocessing the time series before generating the phase projected signal. Preprocessing the time series may comprise using a detrending filter on the time series.

In one or more implementations, the reference signal has a fixed sampling rate, and the time series has a variable sampling rate.

In one or more implementations, the phase projected signal has a plurality of data points of the time series across the predefined time period mapped to the predefined phase interval based on the analytic phase.

In one or more implementations, the transform operation is a Hilbert transform.

In one or more implementations, the reference signal is filtered using a band-pass filter or a low-pass filter. The low-pass filter may have a cutoff frequency below 100 Hz, such as a cutoff frequency of 2 Hz.

Various embodiments relate to a method, such as a hypersampling method. The method may be implemented by a computing system with one or more processors. The method may comprise acquiring, via one or more imaging systems, a reference signal and an undersampled time series for a subject. The method may also comprise filtering the reference signal to obtain a monocomponent signal. The method may moreover comprise determining an analytic phase by applying a convolution operation on the monocomponent signal. The method may additionally comprise applying analytic phase projection to combine the time series and the analytic phase of the reference signal into a phase projected signal. The method may further comprise generating a visual representation of the phase projected signal for an imaging application.

In one or more implementations, the convolution operation is a Hilbert transform.

In one or more implementations, the method furthermore comprises preprocessing the time series using a detrending filter before generating the phase projected signal.

In one or more implementations, the reference signal and the undersampled time series are captured during a same time period.

In one or more implementations, filtering the reference signal to obtain the monocomponent signal comprises applying a low-pass filter to the reference signal.

In one or more implementations, the method furthermore comprises filtering the phase projected signal. Filtering the phase projected signal may comprise applying a low-pass filter to the phase projected signal.

Various embodiments of the disclosure relate to a system. The system may comprise one or more sensors configured to obtain physiological data from a subject. The system may also comprise a computing system communicatively coupled to the one or more sensors. The computing system may comprise one or more processors and instructions which, when executed by the one or more processors, cause the one or more processors to perform specific functions. The one or more processors may use the one or more sensors to acquire a reference signal and an undersampled time series of a subject over a predefined time period. The one or more processors may also filter the reference signal to obtain a monocomponent signal. The one or more processors may moreover determine an analytic phase by performing a transform operation on the monocomponent signal. The one or more processors may additionally generate a phase projected signal from the undersampled time series based on the analytic phase. The one or more processors may further display the phase projected signal for an application.

In one or more implementations, the system further comprises instructions which, when executed by the one or more processors, cause the one or more processors to acquire the undersampled time series using an Mill system, and acquire the reference signal using an EEG system.

BRIEF DESCRIPTION OF THE DRAWINGS

The foregoing and other objects, aspects, features, and advantages of the disclosure will become more apparent and better understood by referring to the following description taken in conjunction with the accompanying drawings:

FIGS. 4A-4D depict processing of simulated signals, from a given undersampled signal containing quasi-periodic data to the estimated hypersampled cycle. FIG. 4A depicts time series x(t), FIG. 4B depicts the underlying signal, FIG. 4C depicts phase projection, and FIG. 4D depicts the hypersampled signal and cycle estimate.

FIG. 7A depicts the reference signal (here identical to the underlying, unknown signal to be estimated), the analytic phase, and time series samples, for a short section of the data. FIG. 7B depicts the hypersampled signal (left panel) and the cycle estimate (right panel). FIG. 7C is like FIG. 7A, but with randomly spaced cycles in the underlying signal. FIG. 7D is like FIG. 7B, but for randomly spaced cycles. The cycle estimate still accurately reflects the underlying signal shape in FIG. 7C.

FIG. 8A depicts the reference signal (here identical to the underlying, unknown signal to be estimated), the gating intervals, and time series samples, for a short section of the data. FIG. 8B depicts the gated signal (left panel) and the cycle estimate (right panel). FIG. 8C is like FIG. 8A, but with randomly spaced cycles in the underlying signal. FIG. 8D is like FIG. 8B, but for randomly spaced cycles. The cycle estimate does not accurately reflect the underlying signal shape in FIG. 8C anymore.

DETAILED DESCRIPTION

Figure 1:
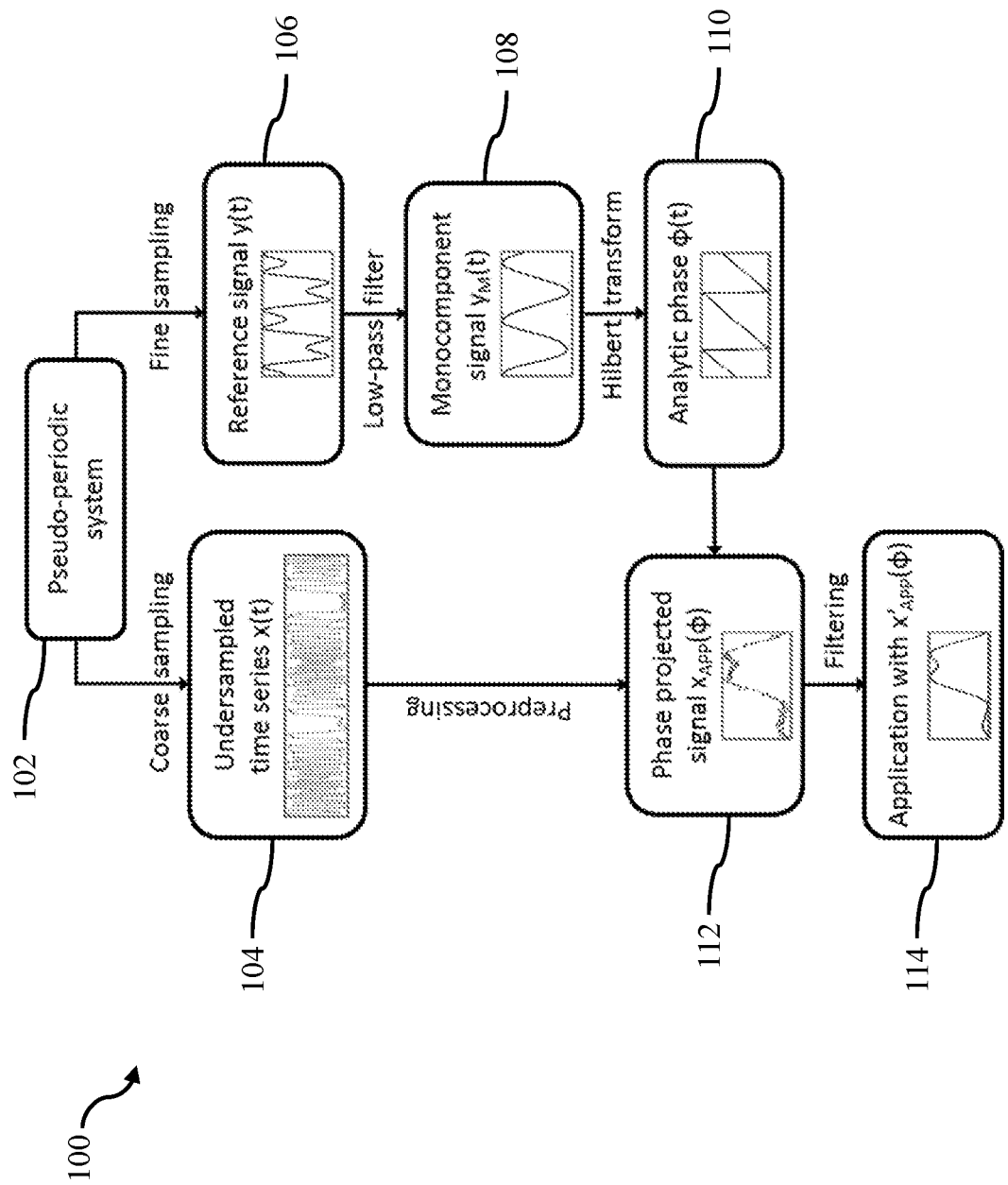
FIG. 1 provides schematics of an analytic phase projection (APP) approach to up-sampling an undersampled signal, according to embodiments of the disclosure.

The various concepts introduced above and discussed in greater detail below may be implemented in any of numerous ways, as the described concepts are not limited to any particular manner of implementation. Examples of specific implementations and applications are provided primarily for illustrative purposes.

Many signals in the biological and biomedical sciences are of a quasi-periodic nature with irregularly spaced, stretched, or otherwise distorted variations of a repeating cycle. An example for a quasi-periodic cycle is the characteristic QRS complex observed in blood pressure signals and electric recordings of the heart. Another example is patterns of electrical activity of the brain observed in electroencephalographic (EEG) surface recordings. Those signals usually can be measured with a sufficient sampling rate to resolve their underlying quasi-periodic cycles (QRS-complex, EEG waveform, respectively). However, often it is not possible to measure the effects of the quasi-periodic dynamics in parts of the body that cannot be accessed so easily, such as deep within the brain.

One method used to obtain signals from anywhere in the brain is frequently magnetic resonance imaging (MRI). Dynamic or functional MRI of the brain is typically sampled at an insufficient rate to resolve the cardiac cycle or EEG patterns. In order to investigate the quasi-periodic signal in a particular location within the brain, one solution is to up-sample the MRI signal at that point with an effective sampling time that is much smaller than the average cardiac cycle or EEG waveform period. The cardiac or EEG recordings then can serve as a reference used to define the quasi-periodicity of the dynamics of interest.

The present disclosure describes systems and methods to up-sample signals by analytic phase projection. The present disclosure replaces the cycle template with a cycle based on the analytic phase of the reference signal, and instead of retrospective gating the time series (numbers or images) are projected onto this so-defined analytic phase. The advantages of the systems and methods of the present disclosure as compared to conventional retrospective gating are manifold.

One advantage includes not entailing the use of a matching template definition for the reference signal. The phase of the reference cycle is rather given by the analytic phase of the reference signal. This will make the method applicable to all problems that require retrospective gating, but with the additional advantage that complex and specific, non-generalizable algorithms to define the template become obsolete. An application reduced to practice is provided below; wave form imaging of cardiac pulse waves in the brain. In this application, an up-sampling factor of brain images of larger than 1000 has been obtained. This high sampling rate allows for the imaging of very fast pulse waves traversing the brain. Pulse waves contain information about vascular integrity, and to be able to measure those in the brain can provide significant clinical information that cannot be obtained by any other method.

Another advantage is that the reference signal may have other temporal characteristics, besides periodic or quasi-periodic. Furthermore, the reference signal may have other spectral characteristics, band-limited, i.e., containing low frequency components of the whole frequency spectrum. Proper filtering then provides a monocomponent reference signal and in turn can provide a well-defined analytic phase. This property lifts a severe restriction of retrospective gating (the quasi-periodicity of signals) and enables new applications where an up-sampling of signals is required. A possible application in which retrospective gating cannot easily but analytic phase projection can be used is the source localization of EEG data of the brain. The EEG reference signal either is already band-limited or can be made band-limited by filtering. The band-limited signal then can be converted into a monocomponent reference signal by further filtering. Source localization can then be obtained by functional Mill time series of the brain projected to the analytic reference phase.

Another advantage is that it is expected that analytic phase projection is more robust with respect to noisy and/or incomplete and/or non-stationary signals than template-based retrospective gating. Again, this will broaden the range of applications considerably.

Up-sampling by analytic phase projection requires a system that provides a reference signal and a system that provides the signal to be up-sampled, as well as software to perform all signal manipulations, and a database to store results. In some embodiments, the data base may be omitted.

Various embodiments of the disclosure relate to methods and systems to up-sample insufficiently sampled time series of quasi-periodic signals. The result may be an estimate of the quasi-periodic cycle underlying the signal. Such "hyper-sampling" may involve a sufficiently sampled reference signal that defines the quasi-periodic dynamics. The time series and reference signal may be combined by projecting the time series values to the analytic phase of the reference signal. The resulting estimate of the quasi-periodic cycle has a considerably higher effective sampling rate than the time series. The procedure may be applied to, for example, time series of MRI images of the human brain. In some implementations, the effective sampling rate could be increased by three orders of magnitude as a result. This allows for capture of the waveforms of the very fast cerebral pulse waves traversing the brain.

FIG. 1 provides an overall summary of hypersampling by APP according to various example embodiments. Two signals may be acquired from a system 102 under study: an undersampled quasi-periodic time series $x(t)$ 104, and a sufficiently sampled quasi-periodic reference signal $y(t)$ 106. The reference signal 106 and the time series 104 may be acquired during the same time interval and may be assumed to have the same quasi-periodicity. Then, a monocomponent signal $y_M(t)$ 108 (box "Monocomponent signal $y_M(t)$") may be obtained by low-pass filtering the reference signal $y(t)$ 106. Monocomponent signals have a monotonically increasing phase. In other words, in a monocomponent signal the instantaneous frequency or time derivative of its phase is non-negative at any time. This phase monotonicity is used later on in the phase projection step, in which the phase is a piecewise invertible function. In some implementations, the phase of a signal is obtained modulo an interval of length $2\pi$, which causes phase resets. At phase resets, the phase has a discontinuity from a value near $\pi$ to a value near $-\pi$, thereby crossing the zero line. The phase is estimated from the monocomponent signal as its analytic phase 110 (box "Analytic phase $\Phi(t)$"; two phase resets are visible). The analytic phase 110 is interpolated to the time series sampling times. Then, the time series values are assigned to their corresponding phase values 112 (box "Phase projected signal $x_{APP}(\Phi)$"). In other words, a coordinate transformation from time to phase is performed: Whereas the original time series depends on time, the phase-projected time series depends on the quasi-periodic cycle phase. In various implementations, the time series values themselves are not altered, they are just re-ordered, thus the description as a "projection." The approach may be referred to as "hypersampling" because the underlying quasi-periodic process is sampled over a time that spans as many quasi-periods as possible in various embodiments. Finally, depending on the particular application, the result may be further filtered in order to obtain an estimate for the phase-projected cycle 114 (box "Application with $x'_{APP}(\Phi)$").

A monocomponent signal can be written as the product of an instantaneous amplitude $\rho(t) \geq 0$ and an instantaneous phase factor $\cos(\Phi(t))$, or as an amplitude-phase modulation. Writing the signal $y_M(t)$ as an amplitude-phase modulation $$y_M(t) = \rho(t)\cos\phi(t), \quad (1)$$

the analytic extension of which is $$y_A(t) = y_M(t) + iy_H(t) = \rho(t)e^{i\phi(t)}, \quad (2)$$

with the Hilbert transform $$y_H(t) = \frac{1}{\pi} P \int_R \frac{y_M(\tau)}{t-\tau} d\tau = \lim_{\varepsilon \to 0^+} \frac{1}{\pi} \int_{|t-\tau|>\varepsilon} \frac{y_M(\tau)}{t-\tau} d\tau. \quad (3)$$

The integral in this expression is a principal value integral. The analytic extension (Eq. 2) expressed via the Hilbert transform (Eq. 3) provides a unique expression for the amplitude-phase modulation (Eq. 1), the canonical amplitude-phase modulation. The Hilbert transform itself can be computed by standard signal processing software. The analytic phase follows from the analytic signal as $$\phi(t) = \arg(y_A(t)) = \arg(y_M(t) + iy_H(t)). \quad (4)$$

The argument function here is the four-quadrant inverse tangent relation, sometimes denoted a tan $2(y_H(t), y_M(t))$. Its principal values are restricted to the interval $(-\pi, \pi]$. In a monocomponent signal, the instantaneous frequency is always non-negative, i.e., $d\Phi(t)/dt \geq 0$, for all time points where it is defined. Thus, the analytic phase is monotonically increasing, and decreasing only during phase resets. The phase monotonicity can be checked either visually by graphing the analytic phase, or automatically by estimating the time derivative of the analytic phase. In the latter case, a sign change of the derivative would indicate non-monotonicity. If necessary, the low-pass filter can be adjusted such as to improve monotonicity of the analytic phase. Depending on the application, it might also be necessary to preprocess the time series, for example to remove trends. Once an approximately monotonic phase of the reference signal has been obtained, the APP can be performed, which combines the time series and the analytic phase of the reference signal.

The (potentially preprocessed) quasi-periodic time series $x(t)$ is sampled at times $t_i$. The sampling times of the analytic phase $\Phi(t)$ are denoted by $\tau_j$. The analytic phase projection is a coordinate transformation of the time series sampling times to the analytic phase, $$\text{APP}: x(t_i) \to x_{APP}(\phi)_i. \quad (5)$$

The index i assumes values from 1 to N, the number of time series samples. Here, $\Phi_i = \Phi(t_i)$ is the analytic phase $\Phi(t)$ numerically interpolated to the signal sampling time $t_i$. This interpolation should be quite accurate in general, as the analytic phase of a monocomponent signal is an approximately smooth function, if sufficiently sampled, except at phase resetting points. For phases near phase reset, the interpolation can become inaccurate and it might be necessary to provide corrective measures, for example discarding outliers. If to each time series sampling time $t_i$ there is a corresponding reference signal sampling time $\tau_j = t_i$, the interpolation step can be omitted, i.e., the phases $\Phi(\tau_j)$ are taken directly as $\Phi_i = \Phi(\tau_j = t_i)$.

The upsampled, phase projected signal $x_{APP}(\Phi)$ is an estimate of the quasi-periodic signal averaged over one period, or, in other words, an estimate of the quasi-periodic cycle. In order to graph this cycle, the phases are ordered from their minimum value near $-\pi$ to their maximum value near $\pi$, and the signal values are ordered accordingly. Whereas the original time series values $x(t)$ depend on time t, the phase projected values $x_{APP}(\Phi)$ depend on phase $\Phi$. Finally, the phase-projected signal can be low-pass filtered in order to remove residual signal components that cannot be accounted for by quasi-periodicity and thus analytic phase projection. The result is a smooth signal estimate $x'_{APP}(\Phi)$. The effective sampling interval of the upsampled signal follows from the number of time series samples, N, and the average quasi-period of the reference signal, T, as $$\Delta T_{\text{eff}} = T/N. \quad (6)$$

This shows that the more samples are measured, the larger the achieved effective sampling rate. Of note, the effective sampling rate does not depend on the original sampling rate of the time series.

Figure 2:
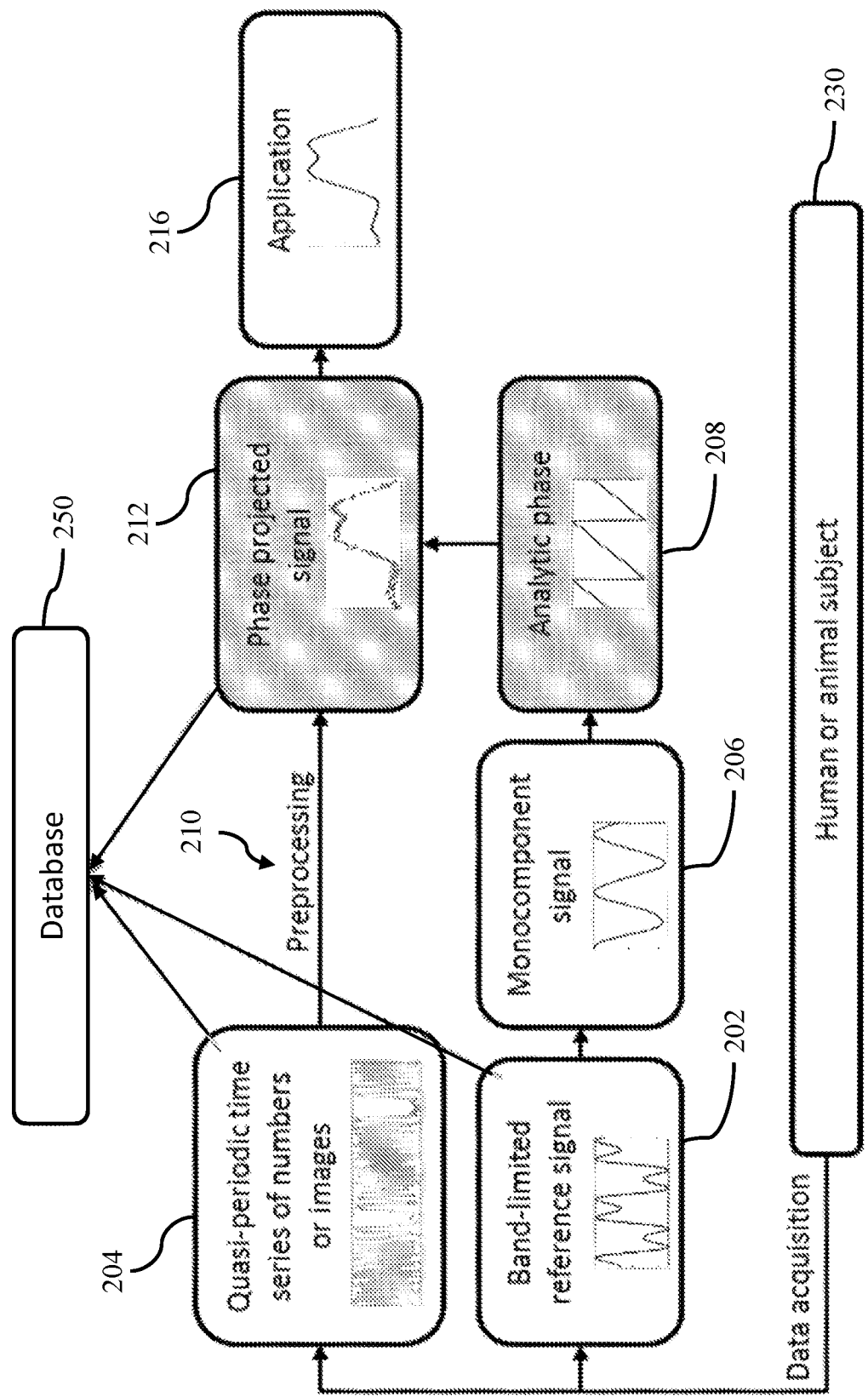
FIG. 2 is a block diagram depicting an illustrative embodiment of systems and methods of performing up-sampling of signals by analytic phase projection.

Referring now to FIG. 2, depicted is a general workflow an example method of performing up-sampling by analytic phase projection according to various embodiments. The method may be implemented using system 900 depicted in FIG. 9 and described below. For example, computations may be performed for processing of signals using signal processor 924. The workflow may include the following steps, and the terminology is defined further below. In brief overview, the method may include (1) A band-limited reference signal is acquired from a subject (e.g., human or animal) (202); (2) simultaneously, a quasi-periodic signal of numbers or images is acquired from the same subject (204); (3) the reference signal is band-pass filtered to obtain a monocomponent signal (206); (4) from the monocomponent signal, the analytic phase is computed via the Hilbert transform (208); (5) the signal of numbers or images is preprocessed and these are procedures to prepare the signal for the next step (210); (6) the preprocessed time series of numbers or images is phase-projected to the analytic phase (212); (7) this results in an up-sampled time series; and (8) the up-sampled signals are used in applications (216).

Analytic phase projection involves the computation of the analytic phase of a monocomponent reference signal by the Hilbert transform. The Hilbert transform itself may be provided by signal processing software (e.g., MATLAB R2017a™ by The MathWorks, Inc.™) or can be programmed for specific applications executable on processors and memory of a computing device. In some embodiments, the Hilbert transform can be replaced by other methods to compute an instantaneous phase and frequency.

In further detail, the "Human or animal subject" 230 is the subject under investigation, from which two signals are acquired: (1) a quasi-periodic time series of numbers or images and (2) a reference signal. In some embodiments, one or more devices with sensors for capturing physiological data can be used to acquire readings from a human or animal subject. In remote applications, the subject may not be present nearby, as the captured data can be transmitted for analysis. In some embodiments, the data may be pre-recorded for future analysis.

The "Quasi-periodic time series of numbers or images" $x(t)$ 204 is a time series that is quasi-periodic and insufficiently sampled. Quasi-periodicity refers to a signal that includes repetitive components of variable length and/or variable spacing in time. The time series can include numbers resulting from a sequential data sampling procedure or of images acquired sequentially over time, containing arrays or volumes of numbers. It is assumed that the quasi-periodicity is such that it cannot be resolved by the sampling of the signal, i.e., the periods of the signal components are typically shorter than the sampling period of the signal used in signal acquisition. In some embodiments, the quasi-periodic time series of numbers or images can be replaced by a partially non-quasi-periodic time series.

The reference signal y(t) is acquired using one or more sensors during the same time interval as x(t) (which may be acquired using a different device) but with a sufficient sampling rate such as to resolve all its features. A low-pass or band-pass filter may be used to filter the reference signal to obtain a monocomponent signal (202). In some embodiments, the band-limited reference signal could be replaced by a not band-limited reference signal and be made band-limited by filtering, or be kept non-band-limited.

The "Monocomponent signal" $y_M(t)$ 206 is the band-pass filtered signal y(t) with the property that its instantaneous frequency does not become negative at any time. In other words, the instantaneous frequency or slope of the analytic phase may increase monotonically in all points where it is defined. (It is not defined during phase resets, where the phase makes a discontinuous jump from a value near π to a value near −π.) Two of these phase resets are visible in FIG. 2 in the box "Analytic phase" φ(t) 208. Specifically, if the signal $y_M(t)$ is written as a canonical amplitude-phase modulation:

$$y_M(t) = \rho(t)\cos \phi(t), \quad (7)$$

its analytic extension is $$A(y)(t) = y_M(t) + iHy_M(t) = \rho(t)e^{i\phi(t)}, \quad (8)$$

with the Hilbert transform $$Hy_M(t) = \frac{1}{\pi} P \int_R \frac{y_M(\tau)}{t-\tau} d\tau = \lim_{\varepsilon \to 0^+} \frac{1}{\pi} \int_{|t-\tau|>\varepsilon} \frac{y_M(\tau)}{t-\tau} d\tau, \quad (9)$$

the instantaneous amplitude p(t), and the "Analytic phase" φ(t) 208. The analytic phase is computed from the analytic signal as $$\phi(t) = \arctan \frac{Hy_M(t)}{y_M(t)}. \quad (10)$$

The instantaneous frequency, the time derivative of the analytic phase, is always non-negative, i.e., dφ(t)/dt≥0, for all time points where it is defined. Thus, the analytic phase is monotonically increasing and decreasing only during phase resets. In some embodiments, there may be numerical solutions to compute the analytic phase that provide a monotonically decreasing rather than increasing phase over time, without affecting the applicability of the present technique. In some embodiments, the analytic phase might be replaced by a non-analytic phase.

The time series of numbers or images may be preprocessed using one or more filters and/or signal processing techniques (e.g., using signal processor 924). The filtering/processing procedures may be used to prepare the time series for processing. A typical preprocessing step may be use of a detrending filter to remove slow signals variability of no interest. In certain implementations, data may be detrended to remove, for example, a linear trend by subtracting the mean or a best-fit line (in the least-squares sense) from the data. In some embodiments, the preprocessing step of the time series may be omitted.

The preprocessed time series and the monocomponent reference signal can be processed to acquire the "Phase projected signal" $x_{APP}(t)$ 212. The analytic phase projection is first described informally and then more formally.

Informally, with respect to analytic phase projection, the reference signal, and the time series that is to be up-sampled, are acquired during the same time interval, but not necessarily at the same sampling rates, because the reference signal is sampled at a higher rate than the time series. Therefore, first the analytic phases of the monocomponent reference signal are interpolated to the time series sampling times. Then, to each time series sampling time there corresponds an analytic phase value, and the time series value at that sampling time is then assigned to that phase value. In other words, a coordinate transformation from time to phase is performed: Whereas the original time series values x(t) depend on time t, the phase projected values $x_{APP}(\varphi)$ depend on phase φ. In this coordinate transformation, all time series sampling times are projected to the phase interval [−π, π]. The values of x do not change in $x_{APP}$, they are just re-ordered, thus the description as a "projection". In some embodiments, the phase projection step can be replaced by projections to a time interval or some other interval rather than a phase interval.

More formally, with respect to the analytic phase projection, the time series under study is denoted by x(t), sampled at times $t_i$. The sampling times of the analytic phase φ(t) are denoted by $\tau_j$. Then the analytic phase projection is a coordinate transformation of the time series sampling times to the analytic phase samples, i.e., $$APP: x(t_i) \to x_{APP}(\phi_i) = x(\phi t_i)). \quad (11)$$

The index i assumes values from 1 to N, the number of time series samples. Here, $\varphi_i = \varphi(t_i)$ is the analytic phase φ(t) numerically interpolated to the signal sampling time $t_i$. This interpolation should be quite accurate in general, as the analytic phase of a monocomponent signal is an overall smooth function, if sufficiently sampled, except at phase resetting points. For phases near phase reset, the interpolation can become inaccurate and it might be necessary to provide corrective measures, for example in order to discard outliers. If to each time series sampling time $t_i$ there is a corresponding reference signal sampling time $\tau_j = t_i$, the interpolation step can be omitted, i.e., the phases $\varphi(\tau_j)$ are taken directly as $\varphi_i = \varphi(\tau_j = t_i)$. To graph the up-sampled, phase projected signal $x_{APP}(\varphi)$, the phases are ordered from their lowest value near −π to their highest value near π, and the signal values are ordered accordingly. This completes the analytic phase projection step.

The effective sampling interval of the up-sampled signal is computed from the number of time series samples in time, N, and the average quasi-period of the time series, T, as $\Delta T_{eff} = T/N$. This shows that the more samples are measured, the larger the achieved effective sampling rate can be. Of note, it does not depend on the original, insufficient, sampling interval of the time series.

If not only a single time series is investigated but a time series of images, this procedure applies to all image components comprising the time series of images. For example, if the time series of images is a time series of three-dimensional images, or volumes, the image components are usually referred to as "voxels." The data set is then given by volumes of voxels, each containing a time series.

During these processing steps, computing system 920 may copy the time series, the reference signal, and the phase-projected signals to a "data base" 250 for further processing and storage.

Finally, the phase-projected signal is used in applications 216. This might involve further processing of the phase-projected signal such as low-pass filtering, in order to remove residual signal components that cannot be accounted for by quasi-periodicity and thus analytic phase projection. This "noise" can then be filtered out to obtain a smooth signal $x'_{APP}(\varphi)$.

Figure 3:
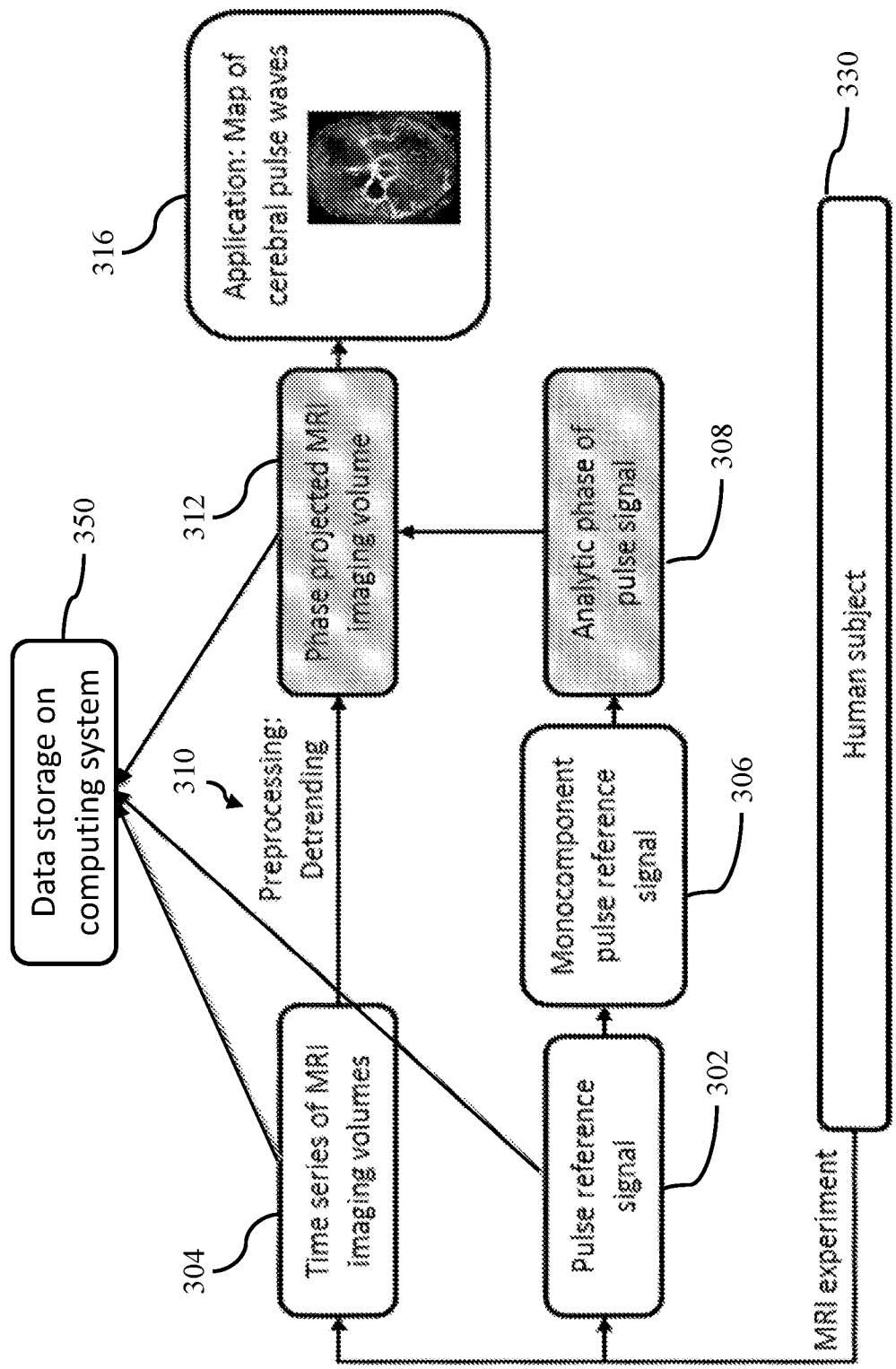
FIG. 3 is a block diagram depicting an illustrative embodiment of systems and methods of performing up-sampling of signals by analytic phase projection for imaging cardiac induced pulse waves in the human brain and measurement of pulse wave velocity.

Referring now to FIG. 3, in some embodiments, the analytic phase projection detailed herein may be used in imaging cardiac induced pulse waves in the human brain and measurement of pulse wave velocity. The present disclosure may be applied to MRI data set that with a sufficiently sampled reference signal, such as the pulse signal of the subject. The Mill data may include a series of hundreds of imaging volumes of a large part of the brain. The procedure applied to this data is summarized in FIG. 3, with numbering of components similar to FIG. 2 to illustrate corresponding components.

In detail, the reference pulse signal first was low-pass filtered in order to obtain a monocomponent signal. The filtered signal is in turn provided a uniquely defined analytic phase obtained by application of the Hilbert transform to the monocomponent reference signal. Then, the time series of MRI images was projected onto the analytic phase. Finally, each MRI analytic phase-projected signal was low-pass filtered to reduce scatter. This provided, for each imaging voxel in the brain imaging volume, a new signal containing the up-sampled time series, which spanned an average cycle of the beating heart. Whereas the original sampling rate of the MRI images was one sample each 2 seconds, the phase-projected time series of images was up-sampled to one sample each 1.8 milliseconds, three orders of magnitude higher than the original sampling rate. This high sampling rate allows for the visualization of vascular waves throughout the brain. The procedure may involve the use of high-resolution data (e.g., data acquired with a sampling time of 2 seconds and a resolution of 1.2 mm).

A signal may be simulated as a nonlinearly transformed chirp signal with linearly increasing frequency from the beginning to the end of the signal time series in order to simulate is sampled at times quasi-periodic data. Added to the data is 10% white noise. Below is provided Matlab script defining the used signals and the analysis in detail. FIG. 4A illustrates the given signal. The sampling time of the signal is 2 seconds. (Artificial physical units are introduced here in order to facilitate comparison with the application to MRI data in the next section.) The signal is undersampled and therefore, the shape of a cycle cannot be recognized from this data. This shape is shown in FIG. 4B (before addition of white noise) and not available to the investigation. The sampling time of the underlying true signal in FIG. 4B is 0.01 seconds, and FIG. 4B, left panel, illustrates that the cycle period at the beginning of the time series is 0.91 seconds. From FIG. 4B, right panel, follows a cycle period of 0.45 seconds, due to the definition of the chirp signal that includes a doubling of frequency from the beginning to the end of the signal.

Figure 4C:
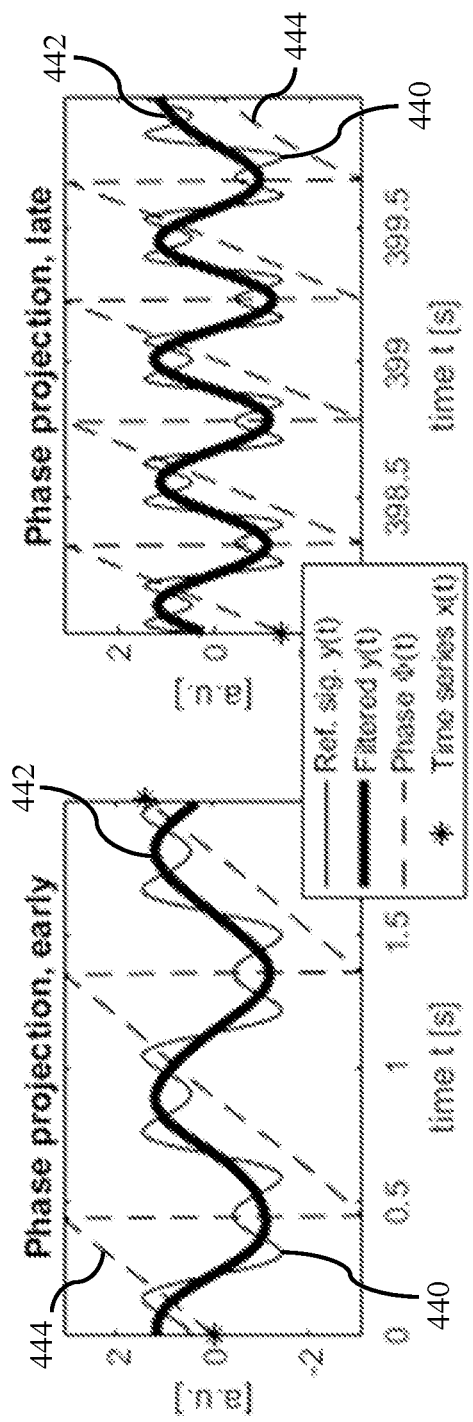
Figure 4D:
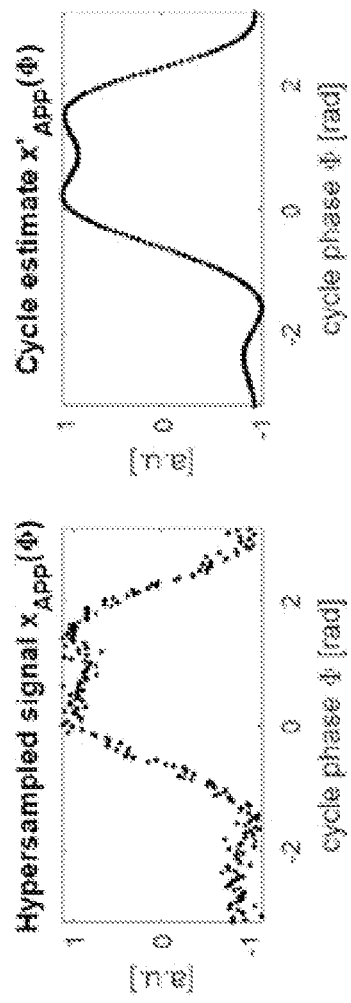

FIG. 4C shows the reference signal in plot 440 and the low-pass filtered reference signal in plot 442, again for the early and late signal portion. The low-pass filtered signal 442 does not show double peaks anymore and is a monocomponent signal. This monocomponent signal enables a monotonic definition of the analytic phase, which is shown in plot 444. The analytic phase is not unwrapped, i.e., only the principal values of the non-invertible arcus tangent relation in Eq. (4) are used. This causes phase resets at the end of each cycle. The first phase reset is seen at a time of 0.44 seconds in FIG. 4C, left panel. Importantly, the analytic phase is well defined both for low frequencies early on in the frequency-swept reference signal and for higher frequencies at the end of the reference signal (left and right panel in FIG. 4C, respectively). In addition, the three sample times of the signal that happen to fall into the shown time intervals via a projection to the analytic phase are marked by an asterisk (*). This is the first part of the phase projection step; the signal sampling times are converted into phases of the cycle. In the final step, all phases are sorted and combined into one cycle. The result of the latter step, the hypersampled cycle, is shown in FIG. 4D, left panel. The noise results mostly from the noise in the noise-contaminated original signal. Application of the same procedure to the underlying non-noisy signal would result in only little scatter, which is due to numerical inaccuracies (not shown). The right panel of FIG. 4D shows a low-pass filtered hypersampled cycle. The right panel of FIG. 4D provides an accurate estimate of the original cycle (compare FIG. 4B, left panel, with FIG. 4D, right panel).

It is important to understand that the phase axis in FIG. 4D does not have a time equivalent. The reason is that the signal includes quasi-periodic cycles of different lengths. However, one can define a "hypersampling rate" as the average sampling rate of the hypersampled cycle. In the present example, the signal contains 662 cycles with lengths from 0.45 to 0.91 seconds resulting from the frequency sweep from 2.21 to 1.10 Hz. With an average cycle length of 0.60 seconds and 200 data points in the original time series, the average sampling interval of the cycle would be about 3 milliseconds (ms). This is a reduction of the original signal sampling interval of 2 seconds by a factor of 662, the number of cycles contained in the time series.

As an example, an application of the disclosed approach to cerebral pulse waves will now be described. Hypersampling via APP is applied to pulse waves in the human brain for studying the properties of cerebral pressure waves and their possible effects on human health. Here, a functional MM scan from a publicly available database is used to demonstrate that hypersampling can resolve pulse waveforms in the brain.

Figure 5A:
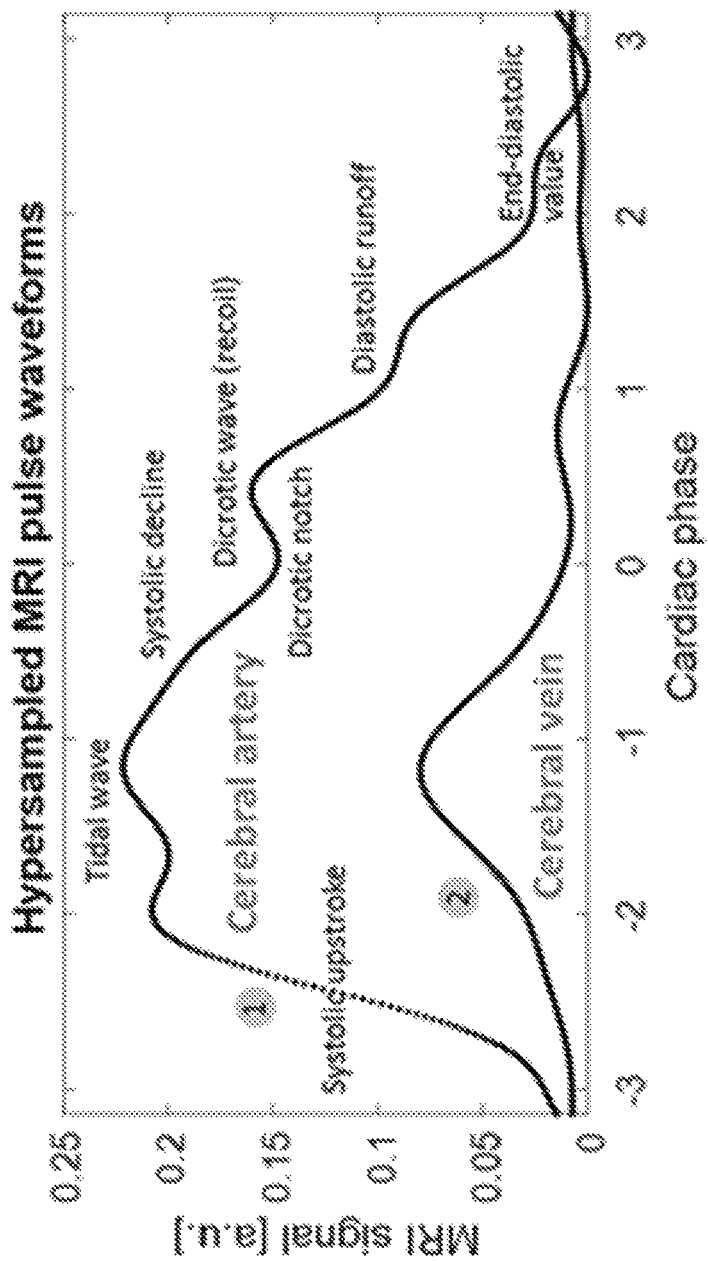
FIGS. 5A-5C illustrate that hypersampled MRI signals of the brain resemble conventional pulse waveforms measured outside of the brain. Waveforms obtained from the middle cerebral artery and the sagittal sinus, a vein (FIG. 5A) and their location in maximum intensity projections of pulse wave amplitude (FIG. 5B, FIG. 5C). Pulse wave amplitudes in panel B are defined as the maximum amplitude difference of the hypersampled waveforms and show mainly arteries. Pulse wave amplitudes in 5C, scaled by the standard deviation of the signal, also show areas with lower pulse wave amplitude, including venous components.
Figures 5B, 5C:
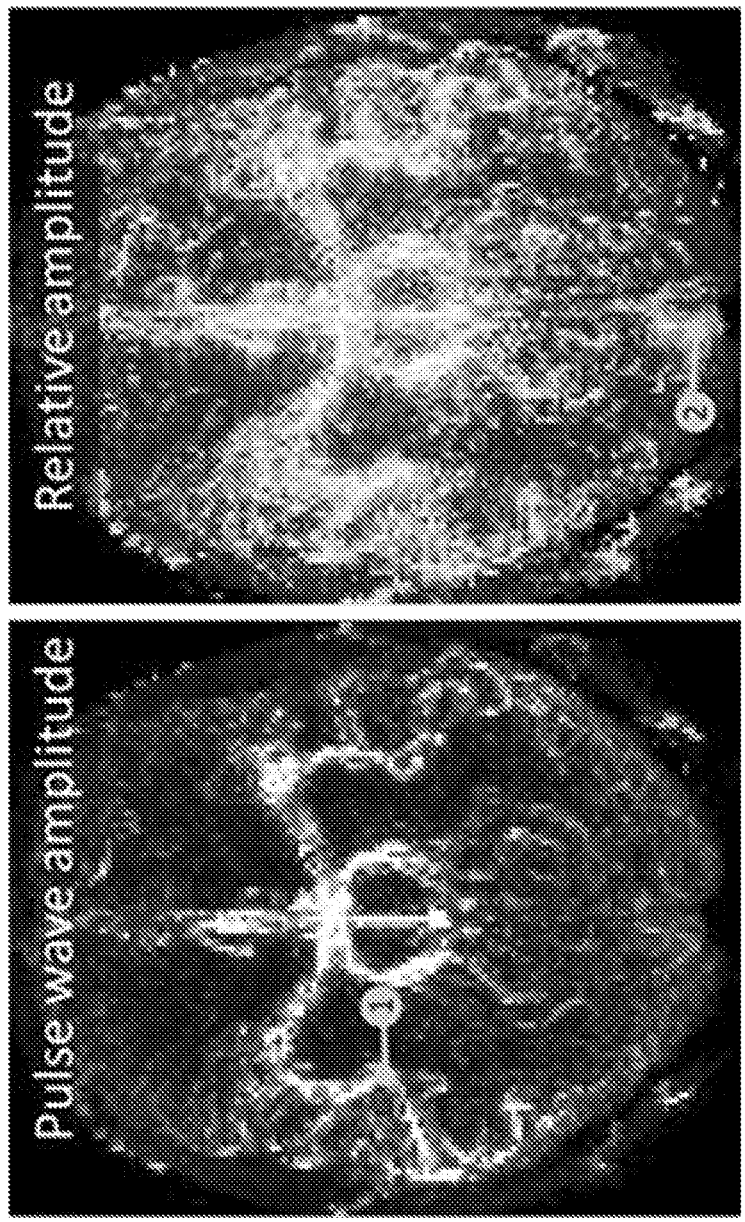

The MRI data includes image volumes covering parts of frontal and occipital cortex and the regions in between, including an area with a dense distribution of main cerebral arteries (see FIG. 5B). The data is sampled every 2 seconds for 15 minutes at 1.2 millimeter (mm) isotropic voxel resolution. The image volumes are not further processed; processed data, such as motion corrected or template-brain-matched data, can cause artifacts that might be detrimental to this analysis. Each voxel in the repeatedly sampled image volume contains a time series of 441 data points.

The reference signal consists of a pulse-oximetry signal acquired on a finger of the subject, sampled with 100 samples per second, or a sampling interval of 10 ms. This is a sufficient sampling rate to define the phase of the underlying quasi-periodic process. The quasi-period of the subject's cardiac dynamics, or the average RR interval, derived from the pulse signal, is 0.856 seconds. This is shorter than the MRI sampling interval of 2 seconds. Therefore, pulse waveforms contained in the MRI signal are not sampled sufficiently to resolve them.

First, the pulse reference signal may be low-pass filtered, by, e.g., using a low-pass filter with a cutoff frequency of 2 Hz, in order to obtain an approximately monocomponent signal. In various implementations, the cutoff frequency for such a cardiac application may be, for example, between 1 and 3 Hz. For other cardiac or non-cardiac applications, the cutoff frequency may be different. For example, for EGG reference signals, the cutoff frequency may be as high as 70 Hz in various embodiments. The approximate monotonicity is validated by visual inspection of the filtered reference signal. Then, the exact acquisition times of the voxels under consideration are computed. This is important, as the whole data volume is acquired sequentially over a time interval of 2 seconds rather than at once. The time series are then high-pass filtered with a cutoff frequency of 0.0042 Hz in order to remove signal trends. The MRI signal is shown with negative sign to account for the fact that blood normally reduces the signal in this kind of MRI, if flow effects can be neglected.

The reference signal contains 1030 cycles. With an average quasi-period of 0.856 seconds and 441 signal samples, the average sampling interval of the cardiac cycle follows from Eq. (6) as $\Delta T_{eff}=1.9$ ms. This is a reduction of the original signal sampling interval of 2 seconds by a factor of 1030, the number of cycles. Note that the original sampling rate of the MRI signal does not enter the calculation of $\Delta T_{eff}$.

Finally, the hypersampled time series is smoothed mildly with a cutoff frequency of 0.0083 Hz in order to remove signal scatter. This is the estimated quasi-periodic cycle, or pulse waveform, in this particular application.

FIG. 5A shows the waveform estimates for a point on the middle cerebral artery, as well as for the sagittal sinus, a vein. These two points are indicated in the pulse amplitude maps in FIGS. 5B and 5C by circled numbers 1 and 2 (①) and (②), respectively. Waveforms obtained from the middle cerebral artery and the sagittal sinus, a vein (FIG. 5A) and their location in maximum intensity projections of pulse wave amplitude (FIG. 5B, FIG. 5C). Pulse wave amplitudes in FIG. 5B are defined as the maximum amplitude difference of the hypersampled waveforms and show mainly arteries. Pulse wave amplitudes in FIG. 5C, scaled by the standard deviation of the signal, also show areas with lower pulse wave amplitude, including venous components. The arterial waveform of FIG. 5A resembles aortic/carotid pulse waveforms, and thus has been annotated with terminology used in conventional pulse wave analysis. The venous waveform is smaller (probably due to attenuation in the capillary bed) and less defined (probably due to dispersion) than the arterial waveform.

Finally, the average lag time between the arterial wave and the outgoing venous wave corresponds to the pulse wave transit time through the brain including the capillary bed. It is estimated as 105 ms, consistent with literature values of cerebral pulse transit times derived from the brain periphery. If the average length of the vascular tree between those two points were known, the pulse wave velocity in the capillary bed could be estimated. Note that the pulse wave velocity is orders of magnitude higher than the blood flow velocity. For comparison, blood transit times would be several seconds.

Referring to FIG. 6A, depicted is an image of the signal variability caused by these waves. As illustrated, the pulse variability map of the human brain obtained from analytic phase projection of an MRI time series of images. The anatomy of main arteries in the brain is clearly visible.

Figure 6:
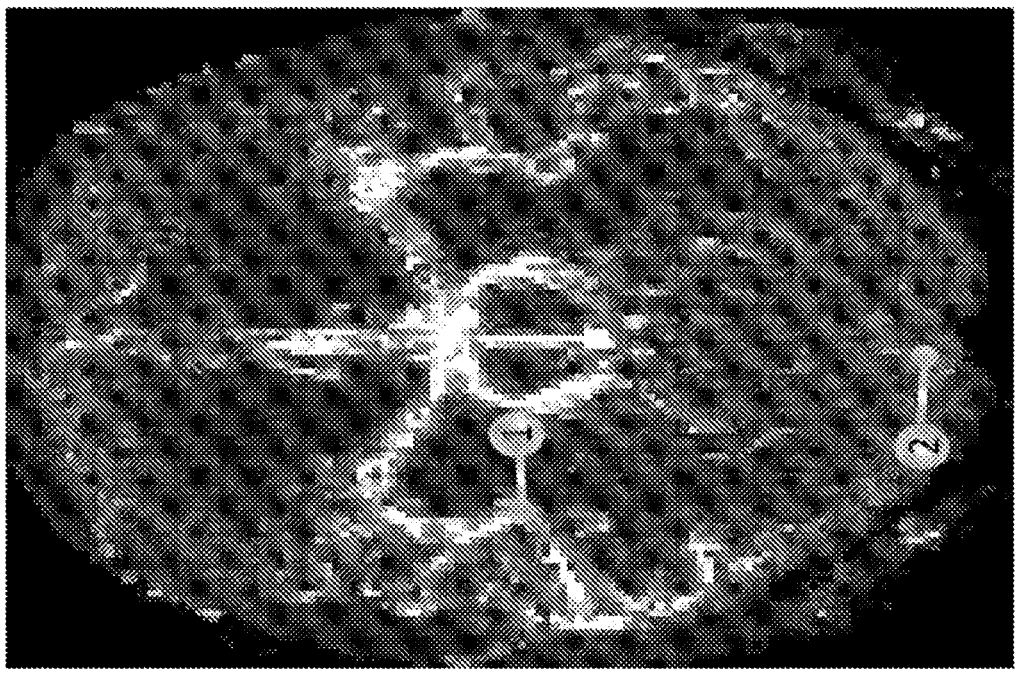
FIG. 6A is a pulse variability map of the human brain obtained from analytic phase projection of an MRI time series of images. A graph of an incoming pulse wave sampled at an artery of the human brain and an outgoing pulse wave sampled at a vein of the human brain is depicted in FIG. 5A.
FIG. 6B is a pulse wave delay map of the human brain between a reference point in the brain and other sample points therein.

Returning to FIG. 5A, shown is the graph of two of those waves, sampled at an artery (incoming pulse wave) and a vein (outgoing pulse wave). For the two points indicated in FIG. 5A, the corresponding up-sampled (phase projected) waveforms are indicated in FIG. 6. Annotations for pulse wave features are provided as well. From the lag between the systolic upstrokes of the cerebral artery (point 1) and the vein (point 2) a pulse traverse time of 105 milliseconds can be measured.

The outgoing wave lags the incoming wave by about 105 milliseconds. This value is consistent with literature values of pulse wave velocities of the brain measured at the periphery by pressure sensors (but not within the brain). The graph shown in FIG. 5A resembles an example of a pressure wave within a peripheral artery (and its features are annotated respectively) but has been obtained from within the brain. As shown, the features of pressure waves observed in the periphery can be reproduced to a large degree within the brain by this method.

Figure 6B:
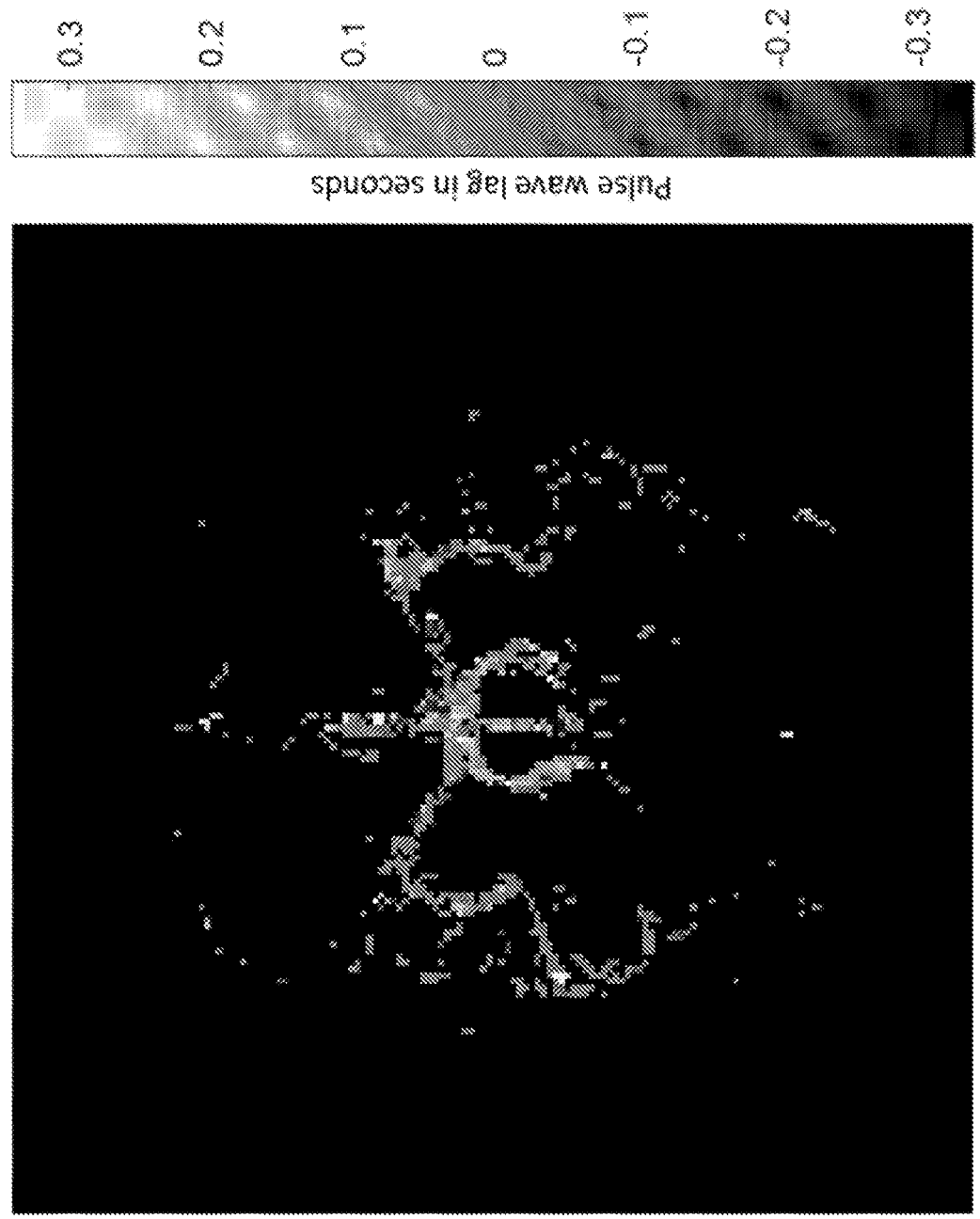

Referring now to FIG. 6B, shown is an example for an application where the signals to be up-sampled are given by a time series of images. The grayscale map provides lag times of traveling pulse waves measured in seconds. An example for the application to a time series of images. Shown is a pulse wave delay map of the brain that encodes the lag between a reference point in the brain (asterisk) and other points in the brain. This lag corresponds to an estimate of the time (in seconds) that the blood pressure wave needs to travel from the reference point to the other points.

In some embodiments, the analytic phase projection detailed herein may be used in up-sampling of functional MM signals by using electrical or optical signals as a reference. Functional MM data of the brain usually is sampled at a rate of one sample each 1 to 4 seconds. These sampling rates are insufficient to match other investigative signals used to understand the brain, such as obtained from electrical and optical experiments. Both electrical (for example, EEG) and optical experiments (for example, diffuse optical tomography and near-infrared spectroscopy) can be performed in humans and animals. In humans, the electric signals can be measured on the surface of the scalp or from electrodes placed within the brain in subjects that have certain diseases such as untreatable epilepsy that warrant such an investigation. Optical signals can be measured from the surface of the scalp. In animals, both methods exist but in addition optical data can also be obtained through the thinned skull, through implanted windows in the skull, on the opened skull, in transparent animals, or from within the brain via fiber optics.

The electric and optical data will be used as reference signals. Often, they are already band-limited, or they can be made band-limited by filtering. From the analytic phase projection of the MM data to the monocomponent reference signals a set of up-sampled MRI time series results that contains quasi-periodic information. These up-sampled signals then can be correlated, voxel by voxel, with the average cycle of the reference signal. This procedure may then provide information about the sources of the electric or optical signals (observed at the surface of the brain, or in case of fiber optics experiments only at distinct points in the brain) within the brain.

This application may provide, in particular, a solution to the important open problem of source localization of EEG data obtained on the scalp or surface of the brain.

In some embodiments, up-sampling by analytic phase projection can be used in imaging and modeling of the cerebrovascular system with potential for applications in biomedical imaging in general and as a biomarker for cerebrovascular disease in particular.

Further possible applications comprise all other applications in which retrospective gating is currently being used. Retrospective gating may be replaced by analytic phase projection in order to become easier to apply (removal of the template-matching step) or for broadened applicability (band-limited reference signals vs. quasi-periodic reference signals, and improved accuracy).

One example may include cardiac imaging. In such applications, the signals to be up-sampled may include biomedical (e.g., MM, CT, PET) images of the beating heart. The reference signal may include the pulse signal (obtained from pulse oximetry or from ECG or another feasible device).

Another example may include functional Mill. In such applications, any functional MRI signals can be up-sampled to a given reference signal. The reference signal can derive from a stimulus of the subject, the cardiac pulse signal, the respiration signal, or any other band-limited signal with a sufficient sampling rate. An example for a stimulus-derived signal could be a movie watched by the subject while in the MRI scanner. If the movie contains a band-limited feature, for example music, this can be converted into a reference signal and the functional response of the brain to this feature can be analyzed by analytic phase projection.

In comparison with retrospective gating, embodiments of the above approach generalize retrospective gating approaches. In most retrospective gating approaches, templates of the reference signal (for example, the R peak of the cardiac cycle) are used to define gating points. A quasi-period, or cycle, is then defined by the interval from one template of the reference signal to the next, for example, RR intervals. Signal sampling times are then linearly projected on cycle times. The analytic phase projection method differs in two points.

First, it defines the quasi-period without use of a template. This might be of particular importance for applications where template fitting could be erroneous, like in respiratory signals with a large variation in amplitude, and EEG signals with a large noise component. In example implementations, the present approach splits the reference signal dynamics into amplitude and phase dynamics, via the Hilbert transform, for example, and then uses the phase evolution for timing. (Other pulse data analysis approaches involving the Hilbert transform do not exploit the monocomponent properties of the signal but rather estimate analytic amplitudes of the signals or their derivatives. Those approaches still require some form of template matching.)

Second, the analytic phase takes account of local nonlinearities of the references signal phase evolution. The projection of time series sampling times to phases does not need to be linear but takes account of the possibly nonlinear cycle dynamics of the reference signal.

Figure 7A:
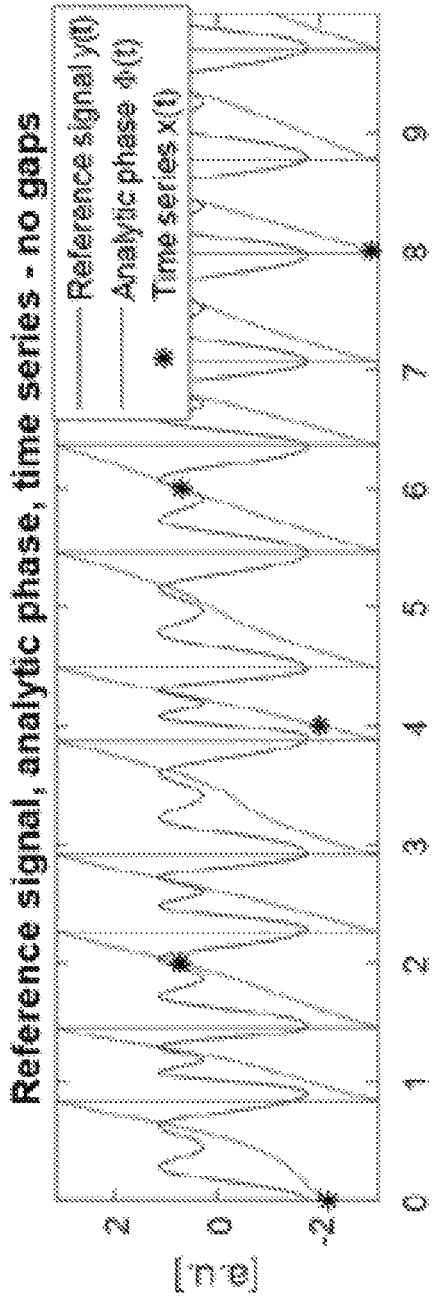
FIGS. 7A-7D depict APP applied to simulated time series.
Figure 7B:
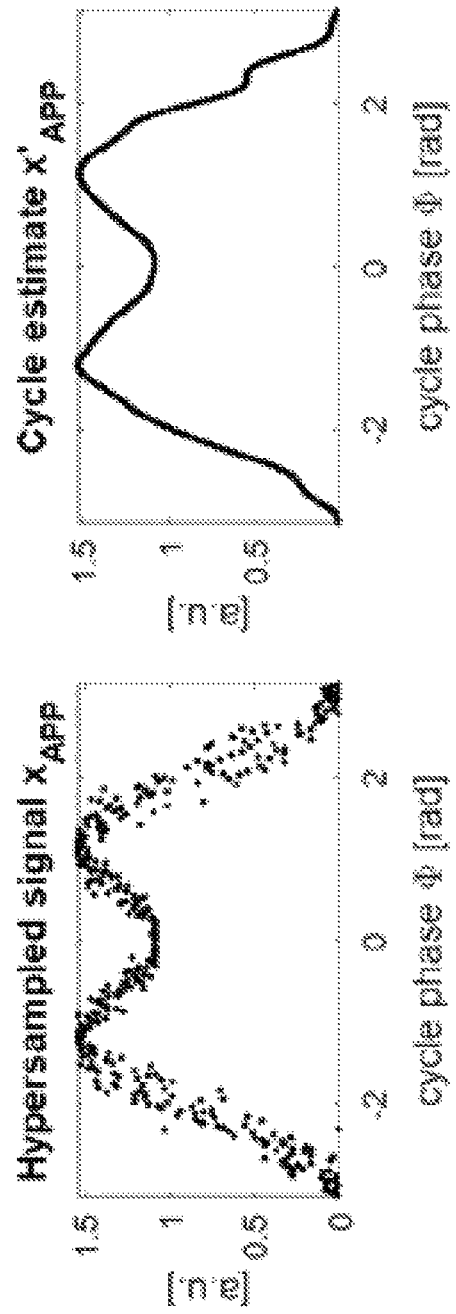
Figure 7C:
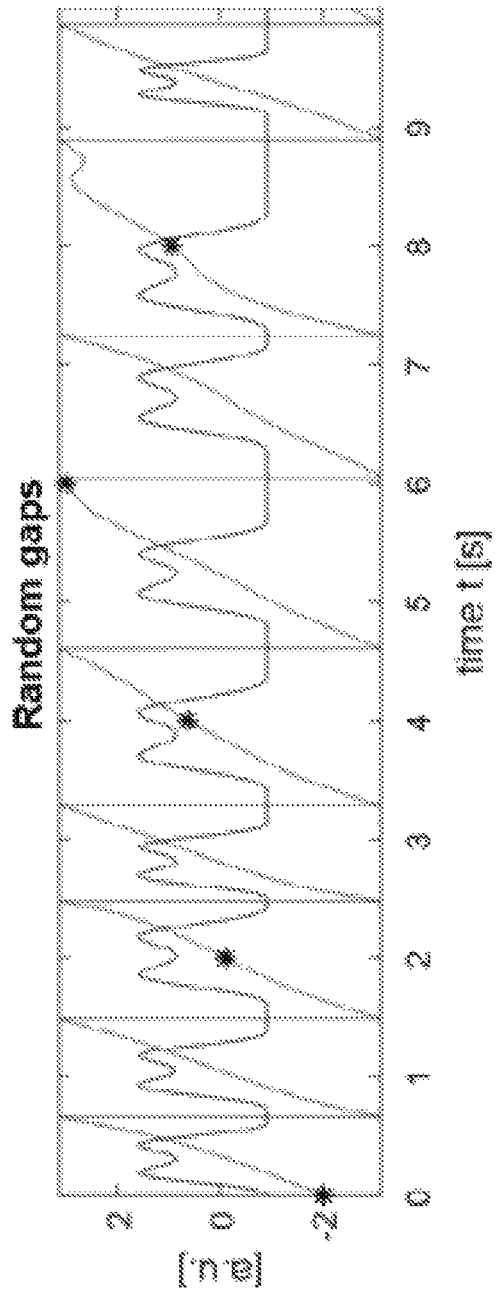
Figure 7D:
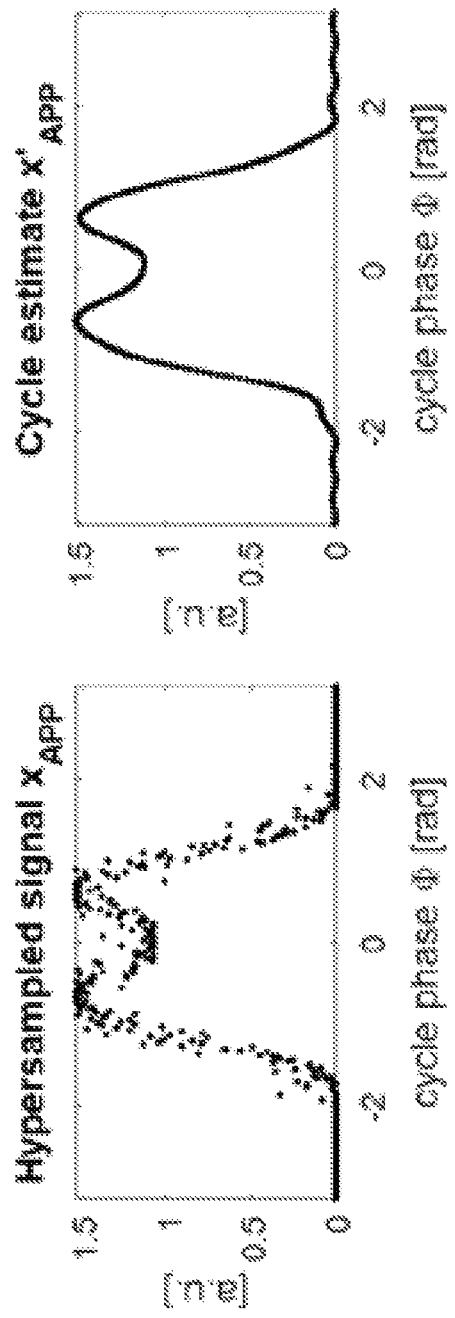
Figure 8A:
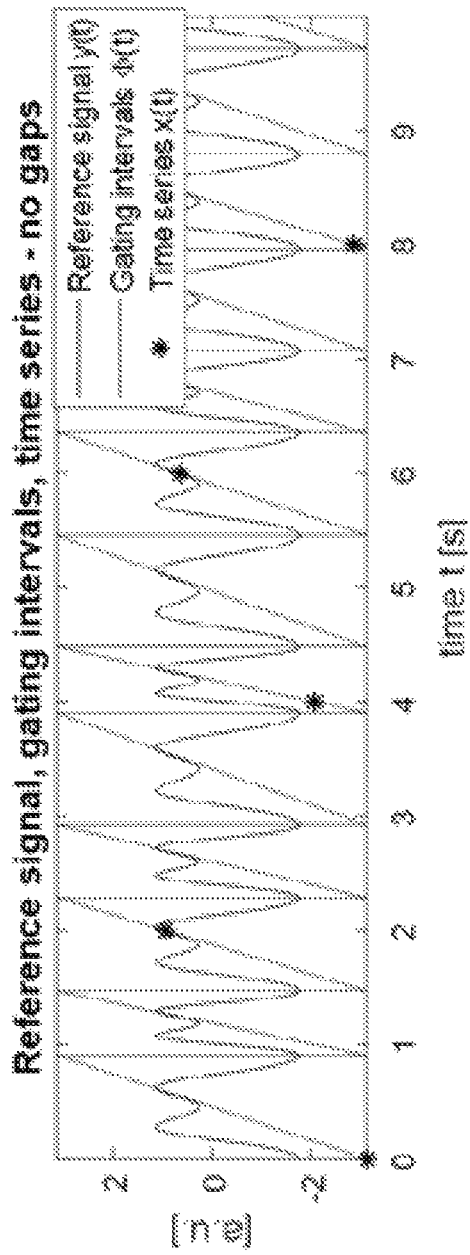
FIGS. 8A-8D depict retrospective gating applied to simulated time series.
Figure 8B:
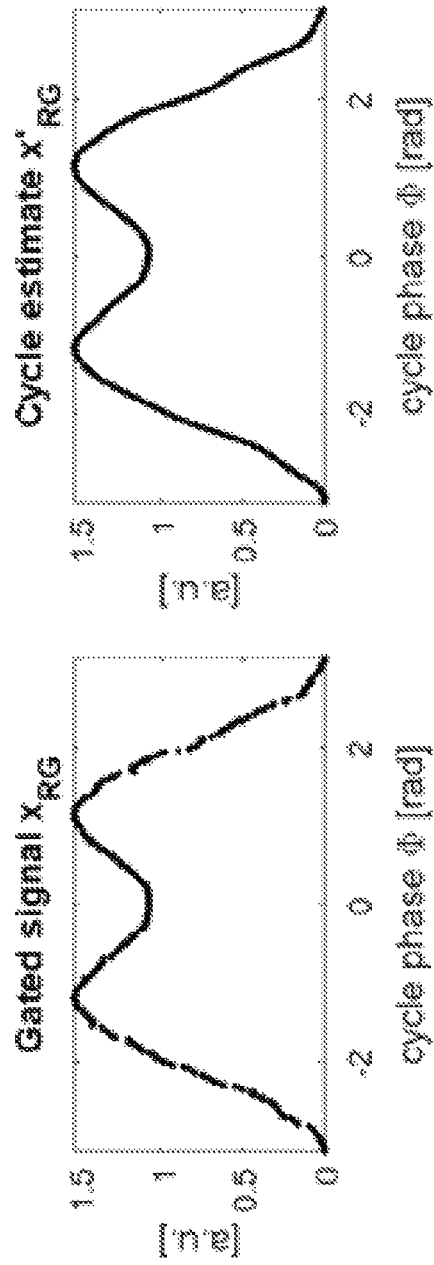
Figure 8C:
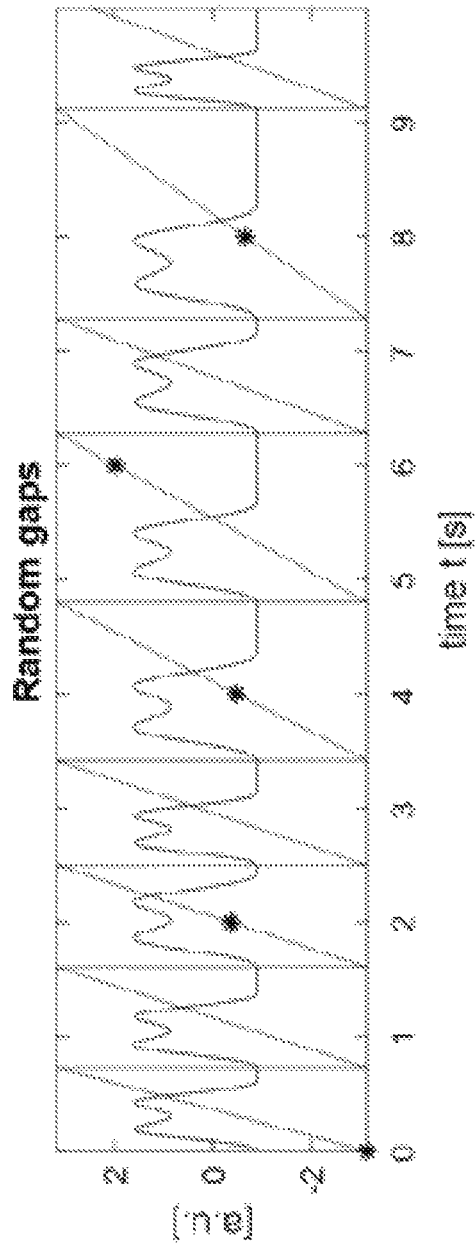
Figure 8D:
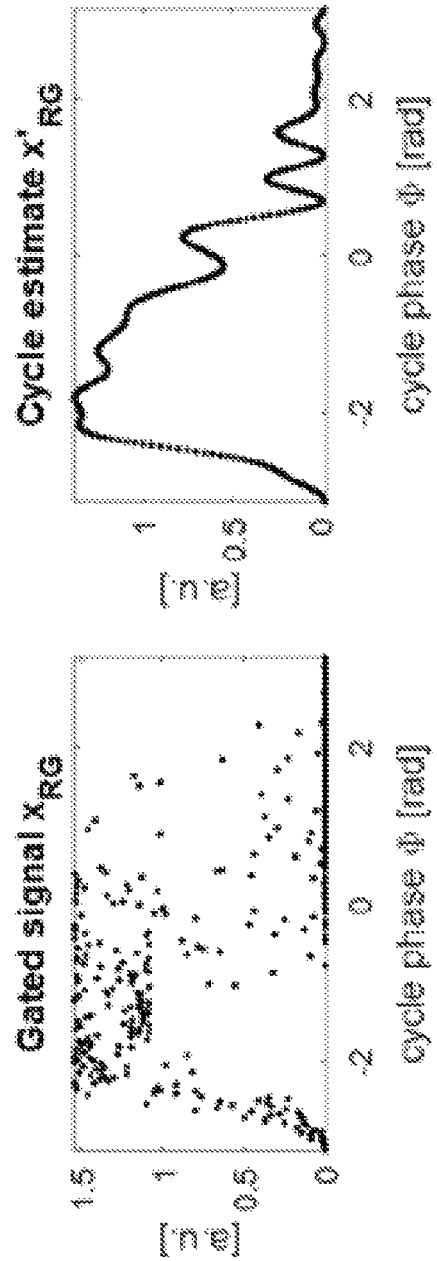

In the following, it is demonstrated on numerical simulations that hypersampling can outperform retrospective gating when the underlying signal phase varies nonlinearly. This is accomplished by first defining a cycle template and then distributing stretched and compressed copies of the cycle template over time with randomly varying intervals, or gaps, between cycles. Such a signal is shown in FIGS. 7C and 8C. Application of hypersampling yields an estimate (FIG. 7D, right panel) that is comparable to the case without random gaps (FIG. 7B, right panel). For the signal of the latter, see FIG. 7A. Comparing these results to the ones in FIGS. 8A-D, retrospective gating, shows that in the case of gaps between the cycles the cycle estimate becomes inaccurate (FIG. 8D, right panel). It does not reflect the situation that there are gaps between the basic cycles, which actually belong to the cycle and make it a cycle with nonlinear phase variation. This phase variation becomes visible in the estimated analytic phase in FIG. $\pi$. This should be compared with FIG. 8C, which shows the linear gating intervals analogously to the phase.

In FIG. $\pi$, it can be seen that the filtering to obtain a monocomponent signal was not sufficient; there is a short interval with negative slope of the phase starting at around 8.5 seconds. This contributes to the scatter of the hyper-sampled signals (FIGS. 7B, 7D, left panels). This scatter actually can be worse than for retrospective gating in case of phase linearity (FIG. 8B, left panel).

For various potential clinical applications, the results of FIGS. 5A-5C, namely the clear identification of characteristic waveforms resembling aortic or carotid blood pressure waves, makes the MRI signal amenable to established procedures of waveform analysis, applied now to cerebral pulse waveforms. The MM signal units are denoted here as "arbitrary" as a clear relationship to blood volume, pressure, flow, and MRI scan parameters is still an ongoing research effort. However, as any MRI signal is proportional to the imaged number of excited hydrogen spins, the blood volume is expected to be a dominant signal generating parameter. Blood pressure p and volume V in arteries are related by the arterial compliance $C(p)=dV(p)/dp$. For low pressure, the compliance is approximately constant, and thus the volume proportional to pressure. The compliance then levels off for larger pressure, depending on the arterial stiffness. Therefore, the observed waveforms could be an approximation for intracranial blood pressure within the linear regime. In addition, some analysis methods of arterial waveforms do not require absolute blood pressure values, for example methods that use the slopes of pressure over time or the timing of peaks/troughs.

Those methods could readily be applied to the hyper-sampled intracranial waveforms to investigate the status of the cerebrovascular system. The pulse transit time from the middle cerebral artery to the sagittal sinus estimated here already contains information of average pulse wave velocity and traveled distance. Whereas conventional (e.g., aortic) pulse wave analysis mainly focuses on cardiac conditions, cerebral pulse wave analysis would be concerned with local as well as downstream conditions in the brain. In particular, small arterioles and capillaries, which are too small to be resolved directly by MRI, might affect the pulse waveforms in the main cerebral arteries via reflection or impedance mismatch effects. This way, measuring cerebral pulse waves via MM hypersampling might open up new avenues for clinical brain imaging.

With respect to EEG source localization, the EEG signal often consists of waveforms with a periodic or quasi-periodic rhythm. Some of the more persistent rhythms, such as alpha, beta, and delta waves, could allow for a similar analysis as the pulse waveform analysis described here. Hypersampling of the MRI signal would be performed as above but with a simultaneously acquired EEG signal as the reference. A possible goal would be to localize the sources of these waveforms in the brain. The MM signal in such a case may reflect these relatively fast oscillations.

Figure 9:
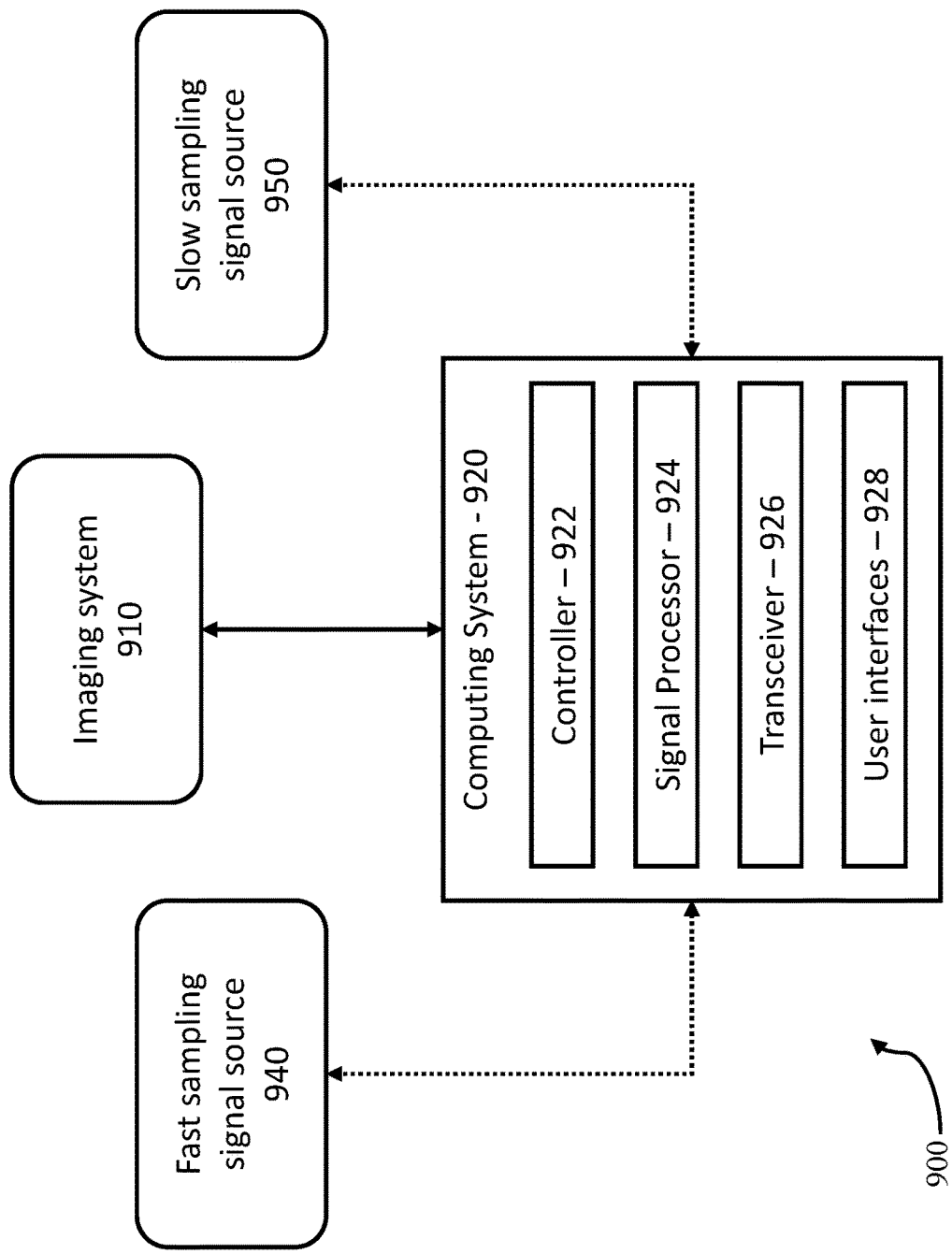
FIG. 9 depicts an example system for implementing disclosed up-sampling approaches according to various embodiments.

Referring to FIG. 9, in various implementations, a hyper-sampling by APP system 900 may include an imaging system 910, or it may be a hybrid imaging system that includes a relatively fast 940 and a relatively slow 950 sampling component. For example, the combination of MRI with optical imaging methods such as multiphoton microscopy would provide a slowly sampled MRI signal and a faster sampled optical signal. The optical signal can then be used as the reference signal to detect the fast component in the MRI signal via APP. In system 900 of FIG. 9, a computing system 920 (or multiple computing systems) may be used to control and/or receive signals acquired via imaging system 910 and/or imaging systems 940 and 950. The computing system may include one or more processors and one or more volatile and non-volatile memories for storing computing code, captured data, etc. The computing system 920 may include one or more databases for storing, for example, signals acquired via one or more sensors. The computing system 920 may include a controller 922 that is capable of exchanging control signals with imaging systems 910, 940, and 950, allowing the computing system 920 to be used to control the capture of images/signals via the sensors thereof. The computing system may also include a signal processor 924 that performs the computations and analyses discussed above using data from imaging systems 910, 940, and 950. A transceiver 926 allows the computing system 920 to exchange readings, control commands, and/or other data with imaging systems 910, 940, and 950, wirelessly or via wires. One or more user interfaces 928 allow the computing system to receive user inputs (e.g., via a keyboard, touchscreen, microphone, camera, etc.) and provide outputs (e.g., via a display screen, audio speakers, etc.).

In various embodiments, an algorithm to upsample an insufficiently sampled quasi-periodic signal with the help of a reference signal, "hypersampling" has been presented. Hypersampling is based on a projection of the signal time series to the analytic phase of the reference signal. Hypersampling has been validated in numerical simulations of quasi-periodic signals, and it has been discussed that in the case of nonlinear phase evolution, hypersampling can outperform retrospective gating. Finally, hypersampling has been applied to dynamic MRI data of the human brain, showing a detailed MRI-measured pulse waveform traversing the brain. Additional applications include source localization of EEG patterns and hybrid imaging systems.

As noted, an "undersampled" signal is a signal with a sampling rate that is not sufficient to resolve the time variability of an object under investigation. For example, in various embodiments, if a signal related to the beating heart is sampled with MRI, the sampling rate is often lower than one sample per second. To resolve the beating heart dynamics, however, the signal may be at least sampled with several samples per second.

An example script that can be used to reproduce the results depicted in FIGS. 4A to 4D will now be presented. This script can be executed using MATLAB R2017a (The MathWorks, Inc., Natick, MA) with the Signal Processing Toolbox by copying it into the Matlab editor.

```
% Numerical simulation of Analytic Phase Projection.
% Definitions
% Signal x(t)
dT=2;
N=200;
period_x=exp(1)/3; % Quasi-period of irregular cyclic
    data
timeaxis_x=transpose((0:N−1)*dT);
f_x=1/period_x; % Frequency of wave
T=N*dT; % Common end time for x, xU, y
f0=f_x; % Chirp signal frequencies
f1=2*f0;
x=chirp(timeaxis_x,f0,T,f1,'linear');
x=sin(0.7*pi*x); % Define double peaks
rng(0);
x=x+0.1*std(x)*randn(N,1); % Add noise
% Upsampled time axis in order to see waveforms.
% Must not be used for analysis
dt=0.01; % Sampling time, same as for y(t)
Ufactor=round(dT/dt); % Upsampling factor
dTU=dT/Ufactor; % 2 ms
NU=N*Ufactor;
timeaxis_xU=transpose((0:NU−1)*dTU);
xU=chirp(timeaxis_xU,f0,T,f1,'linear'); % Upsampled
    signal
xU=sin(0.7*pi*xU); % Double peaks by nonlin. transform.
% Reference data y(t).
% The same frequency as in the signal has to be used
n=N*dT/dt;
timeaxis_y=transpose((0:n−1)*dt);
y=chirp(timeaxis_y,f0,T,f1,'linear');
y=sin(0.9*pi*y); % Double peaks. Eq. can differ from x(t)
% Computations
y=(y−mean(y))/std(y); % Normalization
% Step 1: Obtain monocomponent signal
filHz=3;
ts=timeseries((0:n−1),(0:n−1)*dt); % timeseries(data,
    time)
ts.Data=y;
tmp=idealfilter(ts,[filHz, 1e4],'notch');
y_f=tmp.Data;
% Step 2: Computation of analytic signal
xh=imag(hilbert(y_f));
phi_f=a tan 2(xh,y_f);
% Upsampling factor equals #cycles
numberofcycles=sum(abs(phi_f(2:end)−phi_f(1:end−
    1))>1.8*pi);
RR=N*dT/numberofcycles;
effectedT=RR/N;
disp(['Upsampling factor='num2str(dT/effectivedT)])
% Step 3: Analytic phase association
inter_phi_f=interp1(timeaxis_y,phi_f,timeaxis_x);
% Step 4: Creating phase axis (sorting phases)
[phi_f_projected, index]=sort(inter_phi_f);
% Step 5: Analytic phase projection
xAPP=x(index);
% Step 6: Temporal smoothing
xAPP0=xAPP;
smoo_par=1/60;
ts2=timeseries((0:N−1),(0:N−1)*dT); % timeseries(data,
    time)
ts2.Data=xAPP;
meanvalue=mean(ts2.Data);
tmp=idealfilter(ts2,[smoo_par,1e4],'notch');
xAPP=tmp.Data+meanvalue;
% Figure
figure('position',[100,200,2*300,2*400], 'PaperOrienta-
    tion','portrait');
phi_axis=(timeaxis_x/timeaxis_x(end)−0.5)*2*pi;
xAPP0_plot=xAPP0;
xAPP_plot=xAPP;
% Correct for arbitrary phase shift
xAPP0_plot=circshift(xAPP0_plot,20);
xAPP_plot=circshift(xAPP_plot,20);
subplot(4,2,[1,2])
plot(timeaxis_x,x,'k.-','markersize',10);
axis tight
title('Time series x(t)')
xlabel('time t [s]')
ylabel('x(t) [a.u.]')
subplot(4,2,3)
range1=35:35+90−1;
plot(timeaxis_xU(range1),xU(range1),'k-','linewidth',
    1.5);
```

```
axis tight
title('Underlying signal, early')
xlabel('time t [s]')
ylabel('x(t) [a.u.]')
hold on
subplot(4,2,4)
range2=(length(xU)-90+1):length(xU);
plot(timeaxis_xU(range2),xU(range2),'k-','linewidth',
    1.5);
axis tight
title('Underlying signal, late')
xlabel('time t [s]')
ylabel('x(t) [a.u.]')
hold off
subplot(4,2,5)
range1=1:Ufactor;
plot(timeaxis_y(range1),y(range1),'k-');
hold on
plot(timeaxis_y(range1),y_f(range1),'b-');
plot(timeaxis_y(range1),phi_f(range1),'r-');
range3=1:dT;
plot(timeaxis_x(range3),inter_phi_f(range3),'k*');
axis tight
title('Phase projection, early')
xlabel('time t [s]')
ylabel('[a.u.]')
hold on
subplot(4,2,6)
range2=(length(y)-Ufactor+1):length(y);
plot(timeaxis_y(range2),y(range2),'k-');
hold on
plot(timeaxis_y(range2),y_f(range2),'b-');
plot(timeaxis_y(range2),phi_f(range2),'r-');
range4=N:N;
plot(timeaxis_x(range4),inter_phi_f(range4),'k*');
axis tight
axis tight
legend('Ref. sig. y(t)','Filtered y(t)',
    'Phase \Phi(t)', 'Time series x(t)')
title('Phase projection, late')
xlabel('time t [s]')
ylabel('[a.u.]')
hold off
subplot(4,2,7)
plot(phi_axis,xAPP0_plot,'k.')
axis tight
xlabel('cycle phase \Phi [rad]')
ylabel('[a.u.]')
title('Hypersampled signal x_{APP}(\Phi)')
hold off
subplot(4,2,8)
plot(phi_axis,xAPP_plot,'k.')
axis tight
xlabel('cycle phase \Phi [rad]')
ylabel('[a.u.]')
title('Cycle estimate x"_{APP}(\Phi)')
hold off
```

Non-limiting examples of various embodiments are disclosed herein. Features from one embodiments disclosed herein may be combined with features of another embodiment disclosed herein as someone of ordinary skill in the art would understand.

As utilized herein, the terms "approximately," "about," "substantially" and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described without restricting the scope of these features to the precise numerical ranges provided. Accordingly, these terms should be interpreted as indicating that insubstantial or inconsequential modifications or alterations of the subject matter described and are considered to be within the scope of the disclosure.

For the purpose of this disclosure, the term "coupled" means the joining of two members directly or indirectly to one another. Physical joining may be stationary or moveable in nature. Such joining may be achieved with the two members or the two members and any additional intermediate members being integrally formed as a single unitary body with one another or with the two members or the two members and any additional intermediate members being attached to one another. Such joining may be permanent in nature or may be removable or releasable in nature. Communicative coupling involves the ability to communicate to exchange data, such as commands, instructions to perform functions or operations, data captured using devices with sensors, etc. Data may be exchanged wireless or via wires.

It should be noted that the orientation of various elements may differ according to other exemplary embodiments, and that such variations are intended to be encompassed by the present disclosure. It is recognized that features of the disclosed embodiments can be incorporated into other disclosed embodiments.

It is important to note that the constructions and arrangements of apparatuses or the components thereof as shown in the various exemplary embodiments are illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter disclosed. For example, elements shown as integrally formed may be constructed of multiple parts or elements, the position of elements may be reversed or otherwise varied, and the nature or number of discrete elements or positions may be altered or varied. The order or sequence of any process or method steps may be varied or re-sequenced according to alternative embodiments. Other substitutions, modifications, changes and omissions may also be made in the design, operating conditions and arrangement of the various exemplary embodiments without departing from the scope of the present disclosure.

While various inventive embodiments have been described and illustrated herein, those of ordinary skill in the art will readily envision a variety of other mechanisms and/or structures for performing the function and/or obtaining the results and/or one or more of the advantages described herein, and each of such variations and/or modifications is deemed to be within the scope of the inventive embodiments described herein. More generally, those skilled in the art will readily appreciate that, unless otherwise noted, any parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, the technology described herein may be embodied as a method, of which at least one example has been provided. The acts performed as part of the method may be ordered in any suitable way unless otherwise specifically noted. Accordingly, embodiments may be constructed in which acts are performed in an order different than illustrated, which may include performing some acts simultaneously, even though shown as sequential acts in illustrative embodiments.

The indefinite articles "a" and "an," as used herein in the specification and in the claims, unless clearly indicated to the contrary, should be understood to mean "at least one." As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of" will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of" "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Embodiments of the present disclosure can be realized using any combination of dedicated components and/or programmable processors and/or other programmable devices. The various processes described herein can be implemented on the same processor or different processors in any combination. Where components are described as being configured to perform certain operations, such configuration can be accomplished, e.g., by designing electronic circuits to perform the operation, by programming programmable electronic circuits (such as microprocessors) to perform the operation, or any combination thereof. Further, while the embodiments described above may make reference to specific hardware and software components, those skilled in the art will appreciate that different combinations of hardware and/or software components may also be used and that particular operations described as being implemented in hardware might also be implemented in software or vice versa.

Computer programs incorporating various features of the present disclosure may be encoded and stored on various computer readable storage media; suitable media include magnetic disk or tape, optical storage media such as compact disk (CD) or DVD (digital versatile disk), flash memory, and other non-transitory media. Computer readable media encoded with the program code may be packaged with a compatible electronic device, or the program code may be provided separately from electronic devices (e.g., via Internet download or as a separately packaged computer-readable storage medium).

Embodiments of the disclosure relate to a non-transitory computer-readable storage medium having computer code thereon for performing various computer-implemented operations. The term "computer-readable storage medium" is used herein to include any medium that is capable of storing or encoding a sequence of instructions or computer codes for performing the operations, methodologies, and techniques described herein. The media and computer code may be those specially designed and constructed for the purposes of the embodiments of the disclosure, or they may be of the kind well known and available to those having skill in the computer software arts. Examples of computer-readable storage media include, but are not limited to: magnetic media such as hard disks, floppy disks, and magnetic tape; optical media such as CD-ROMs and holographic devices; magneto-optical media such as optical disks; and hardware devices that are specially configured to store and execute program code, such as application-specific integrated circuits (ASICs), programmable logic devices (PLDs), and ROM and RAM devices.

Examples of computer code include machine code, such as produced by a compiler, and files containing higher-level code that are executed by a computer using an interpreter or a compiler. For example, an embodiment of the disclosure may be implemented using Java, C++, or other object-oriented programming language and development tools. Additional examples of computer code include encrypted code and compressed code. Moreover, an embodiment of the disclosure may be downloaded as a computer program product, which may be transferred from a remote computer (e.g., a server computer) to a requesting computer (e.g., a client computer or a different server computer) via a transmission channel. Another embodiment of the disclosure may be implemented in hardwired circuitry in place of, or in combination with, machine-executable software instructions.

Although the disclosure has been described with respect to specific embodiments, it will be appreciated that the disclosure is intended to cover all modifications and equivalents within the scope of the following claims.

What is claimed:

1. A method of imaging a subject via analytic phase projection, the method comprising:
acquiring, by a computing device including one or more processors, physiological data of the subject over a predetermined time period, the physiological data comprising (i) a reference signal from a first system, and (ii) a time series of numbers or images from a second system, wherein the reference signal comprises a plurality of periods of a quasi-periodic process, and wherein the time series of numbers or images corresponds to an unordered sequence of images of the quasi-periodic process;
filtering, by the computing device, the reference signal to obtain a monocomponent signal;
determining, by the computing device, by performing a transform operation on the monocomponent signal, an analytic phase;
generating, by the computing device, a phase projected signal from the time series of numbers or images based on the analytic phase, wherein generating the phase projected signal reorders the unordered sequence of images to time-resolve the quasi-periodic process;
rendering, by the computing system, based at least in part on the phase projected signal, an ordered sequence of images corresponding to the quasi-periodic process; and
displaying, by the computing device, the ordered sequence of images to visually depict the quasi-periodic process.

2. The method of claim 1, wherein the ordered sequence of images is displayed as a movie representing a period of the quasi-periodic process.

3. The method of claim 1, wherein the time series and the reference signal are acquired during a predefined time interval.

4. The method of claim 1, further comprising preprocessing the time series before generating the phase projected signal.

5. The method of claim 4, wherein preprocessing the time series comprises using a detrending filter on the time series.

6. The method of claim 1, wherein the reference signal has a fixed sampling rate, and the time series has a variable sampling rate.

7. The method of claim 1, wherein the phase projected signal has a plurality of data points of the time series across the predefined time period mapped to the predefined phase interval based on the analytic phase.

8. The method of claim 1, wherein the transform operation is a Hilbert transform.

9. The method of claim 1, wherein the reference signal is filtered using a band-pass filter.

10. The method of claim 1, wherein the reference signal is filtered using a low-pass filter.

11. The method of claim 10, wherein the low-pass filter has a cutoff frequency below 100 Hz.

12. The method of claim 1, wherein the time series and the reference signal are acquired simultaneously during the predefined time interval.

13. The method of claim 1, wherein the analytic phase is based on a trigonometric function of a ratio of the monocomponent signal to a transform of the monocomponent signal.

14. The method of claim 13, wherein the trigonometric function is an arctangent, and wherein the transform is a Hilbert transform.

15. The method of claim 1,
wherein the first system comprises an EEG system, an ECG system, or a pulse oximetry system, and
wherein the second system comprises a biomedical imager selected from a group consisting of an MRI system, a CT system, and a PET system.

16. A method of imaging a subject, the method comprising:
acquiring for the subject, by one or more processors, a reference signal using a first system and an undersampled time series using a second system, wherein the reference signal comprises a plurality of periods of a quasi-periodic process, and wherein the time series comprises a time series of numbers or images corresponding to an unordered sequence of images of the quasi-periodic process;
filtering, by the one or more processors, the reference signal to obtain a monocomponent signal;
determining, by the one or more processors, an analytic phase by applying a convolution operation on the monocomponent signal;
applying, by the one or more processors, analytic phase projection to combine the time series and the analytic phase of the reference signal into a phase projected signal, wherein applying the analytic phase projection reorders the unordered sequence of images to time-resolve the quasi-periodic process;
generating, by the one or more processors, a visual representation based at least in part on the phase projected signal, the visual representation comprising an ordered sequence of images corresponding to the quasi-periodic process; and
displaying on a display screen, by the one or more processors, the generated visual representation as a movie depicting the quasi-periodic process.

17. The method of claim 16, wherein the convolution operation is a Hilbert transform.

18. The method of claim 16, further comprising preprocessing the time series using a detrending filter before generating the phase projected signal.

19. The method of claim 16, wherein the reference signal and the undersampled time series are captured during a same time period.

20. The method of claim 16, wherein filtering the reference signal to obtain the monocomponent signal comprises applying a low-pass filter to the reference signal.

21. The method of claim 16, further comprising filtering the phase projected signal.

22. The method of claim 21, wherein filtering the phase projected signal comprises applying a low-pass filter to the phase projected signal.

23. An imaging system comprising:
one or more sensors configured to obtain physiological data of a subject;
a display device; and
a computing system communicatively coupled to the one or more sensors, the computing system having one or more processors and instructions which, when executed by the one or more processors, cause the one or more processors to:
use the one or more sensors to acquire an undersampled time series of a subject over a predefined time period, wherein the time series comprises an unordered sequence of images of a quasi-periodic process;
obtain, from a second system, a reference signal over the predefined time period, wherein the reference signal comprises a plurality of periods of the quasi-periodic process;

filter the reference signal to obtain a monocomponent signal;

determine an analytic phase by performing a transform operation on the monocomponent signal;

generate a phase projected signal from the under-sampled time series based on the analytic phase, wherein generating the phase projected signal reorders the unordered sequence of images to time-resolve the quasi-periodic process;

rendering, based at least in part on the phase projected signal, one or more images of the subject, an ordered sequence of images corresponding to the quasi-periodic process; and display, on the display device, the ordered sequence of images as a movie depicting the quasi-periodic process.

24. The imaging system of claim 23, wherein the imaging system is an MRI system, wherein the second system used to acquire the reference signal is an ECG system, and wherein the quasi-periodic process is a beating heart.

* * * * *